(12) United States Patent
Zhao et al.

(10) Patent No.: US 11,364,156 B2
(45) Date of Patent: Jun. 21, 2022

(54) DISPOSABLE ABSORBENT ARTICLE

(71) Applicant: The Procter & Gamble Company, Cincinnati, OH (US)

(72) Inventors: Jean Jianqun Zhao, Cincinnati, OH (US); John Richard Noel, Cincinnati, OH (US); Karen Denise McAffry, Cincinnati, OH (US); Gary Wayne Gilbertson, Liberty Township, OH (US); Brian Francis Gray, Cincinnati, OH (US); Kelyn Anne Arora, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 936 days.

(21) Appl. No.: 15/291,383

(22) Filed: Oct. 12, 2016

(65) Prior Publication Data

US 2017/0027766 A1 Feb. 2, 2017

Related U.S. Application Data

(63) Continuation of application No. 13/940,653, filed on Jul. 12, 2013, now abandoned, which is a (Continued)

(51) Int. Cl.
*A61F 13/53* (2006.01)
*A61F 13/47* (2006.01)
(Continued)

(52) U.S. Cl.
CPC ........ *A61F 13/47* (2013.01); *A61F 13/15707* (2013.01); *A61F 13/533* (2013.01);
(Continued)

(58) Field of Classification Search
CPC ............ A61F 13/4704; A61F 13/47218; A61F 13/4756; A61F 13/533; A61F 13/536; A61F 2013/53445
See application file for complete search history.

(56) References Cited

U.S. PATENT DOCUMENTS 2,068,456 A  1/1937 Hooper
2,275,425 A  3/1942 Grabec
(Continued)

FOREIGN PATENT DOCUMENTS

EP  0 509 012 B1  7/1995
EP  0 955 159 A1  11/1999
(Continued)

OTHER PUBLICATIONS

PCT International Search Report, dated Apr. 7, 2008.
(Continued)

*Primary Examiner* — Catharine L Anderson
(74) *Attorney, Agent, or Firm* — William E. Gallagher

(57) ABSTRACT

An absorbent article that can be a sanitary napkin. The absorbent article comprises a topsheet joined to a backsheet and has an absorbent core material disposed therebetween, the absorbent core material being a fibrous absorbent material exhibiting on one side thereof discrete raised portions. The raised portions define a continuous network of channels, the channels defining a void region adjacent the topsheet of the sanitary napkin.

20 Claims, 26 Drawing Sheets

Related U.S. Application Data continuation of application No. 11/714,020, filed on Mar. 5, 2007, now Pat. No. 8,502,013.

(51) Int. Cl.
*A61F 13/15* (2006.01)
*A61F 13/533* (2006.01)
*A61F 13/536* (2006.01)

(52) U.S. Cl.
CPC .. *A61F 13/536* (2013.01); *A61F 2013/15422* (2013.01); *A61F 2013/530226* (2013.01); *A61F 2013/530343* (2013.01); *A61F 2013/530437* (2013.01); *A61F 2013/530868* (2013.01)

(56) References Cited

U.S. PATENT DOCUMENTS

| | | | |
|---|---|---|---|
| 2,404,758 A | 7/1946 | Teague et al. | |
| 2,633,441 A | 3/1953 | Buttress | |
| 2,748,863 A | 6/1956 | Benton | |
| 2,924,863 A | 2/1960 | Chavannes | |
| 3,046,986 A | 7/1962 | Harwood | |
| 3,062,379 A | 11/1962 | Bryan | |
| 3,073,304 A | 1/1963 | Schaar | |
| 3,081,500 A | 3/1963 | Griswold et al. | |
| 3,081,512 A | 3/1963 | Griswold | |
| 3,137,893 A | 6/1964 | Gelpke | |
| 3,337,388 A | 8/1967 | Wosaba, II | |
| 3,355,974 A | 12/1967 | Carmichael | |
| 3,505,703 A | 4/1970 | Miller et al. | |
| 3,511,740 A | 5/1970 | Sanders | |
| 3,540,073 A | 11/1970 | Issenmann et al. | |
| 3,542,634 A | 11/1970 | Such et al. | |
| 3,566,726 A | 3/1971 | Politis | |
| 3,579,763 A | 5/1971 | Sommer | |
| 3,681,182 A | 8/1972 | Kalwaites | |
| 3,681,183 A | 8/1972 | Kalwaites | |
| 3,684,284 A | 8/1972 | Tranfield | |
| 3,695,270 A | 10/1972 | Dostal | |
| 3,718,059 A | 2/1973 | Clayton | |
| 3,760,671 A | 9/1973 | Jenkins | |
| 3,881,490 A * | 5/1975 | Whitehead | A61F 13/533 604/366 |
| 3,881,987 A | 5/1975 | Benz | |
| 3,908,659 A | 9/1975 | Wehrmeyer | |
| 3,949,127 A | 4/1976 | Ostermeier et al. | |
| 3,960,652 A | 6/1976 | Conway et al. | |
| 3,965,906 A | 6/1976 | Karami | |
| 3,967,623 A | 7/1976 | Elias et al. | |
| 4,035,881 A | 7/1977 | Zocher et al. | |
| 4,042,453 A | 8/1977 | Conway | |
| 4,135,021 A | 1/1979 | Patchell et al. | |
| 4,260,443 A | 4/1981 | Lindsay et al. | |
| 4,276,336 A | 6/1981 | Sabee | |
| 4,379,799 A | 4/1983 | Holmes | |
| 4,397,644 A | 8/1983 | Matthews et al. | |
| 4,443,512 A | 4/1984 | Delvaux | |
| 4,465,726 A | 8/1984 | Holmes | |
| 4,469,734 A | 9/1984 | Minto et al. | |
| 4,529,480 A | 7/1985 | Trokhan | |
| 4,559,050 A * | 12/1985 | Iskra | A61F 13/15203 604/368 |
| 4,578,068 A | 3/1986 | Kramer et al. | |
| 4,588,630 A | 5/1986 | Shimalla | |
| 4,673,402 A | 6/1987 | Weisman | |
| 4,676,786 A | 6/1987 | Nishino | |
| 4,741,941 A | 5/1988 | Englebert et al. | |
| 4,758,297 A | 7/1988 | Calligarich | |
| 4,781,962 A | 11/1988 | Zamarripa et al. | |
| 4,798,604 A | 1/1989 | Carter | |
| 4,820,294 A | 4/1989 | Morris | |
| 4,840,692 A | 6/1989 | Kamstrup-Larsen | |
| 4,840,829 A | 6/1989 | Suzuki et al. | |
| 4,859,519 A | 8/1989 | Cabe, Jr. et al. | |
| 4,886,632 A | 12/1989 | Van Iten et al. | |
| 4,935,087 A | 6/1990 | Gilman | |
| 4,953,270 A | 9/1990 | Gilpatrick | |
| 5,009,653 A | 4/1991 | Osborn, III | |
| 5,019,062 A | 5/1991 | Ryan et al. | |
| 5,062,418 A | 11/1991 | Dyer | |
| 5,069,676 A * | 12/1991 | Ito | A61F 13/47 604/358 |
| 5,078,710 A | 1/1992 | Suda | |
| 5,144,730 A | 9/1992 | Dilo | |
| 5,165,979 A | 11/1992 | Watkins et al. | |
| 5,171,238 A | 12/1992 | Kajander | |
| 5,180,620 A | 1/1993 | Mende | |
| 5,188,625 A | 2/1993 | Van Iten et al. | |
| 5,223,319 A | 6/1993 | Cotton et al. | |
| 5,242,632 A | 9/1993 | Mende | |
| 5,281,208 A | 1/1994 | Thompson et al. | |
| 5,342,338 A | 8/1994 | Roe | |
| 5,382,245 A | 1/1995 | Thompson | |
| 5,383,870 A | 1/1995 | Takai et al. | |
| 5,387,209 A | 2/1995 | Yamamoto et al. | |
| 5,414,914 A | 5/1995 | Suzuki et al. | |
| 5,415,640 A | 5/1995 | Kirby et al. | |
| 5,429,854 A | 7/1995 | Currie et al. | |
| 5,437,653 A | 8/1995 | Gilman et al. | |
| 5,470,326 A | 11/1995 | Dabi et al. | |
| 5,505,718 A | 4/1996 | Roe et al. | |
| 5,508,080 A | 4/1996 | Sorimachi et al. | |
| 5,518,801 A | 5/1996 | Chappell | |
| 5,533,991 A | 7/1996 | Kirby et al. | |
| 5,536,555 A | 7/1996 | Zelazoski | |
| 5,554,145 A | 9/1996 | Roe | |
| 5,558,655 A | 9/1996 | Jezzi | |
| 5,560,794 A | 10/1996 | Currie et al. | |
| 5,567,501 A | 10/1996 | Srinivasan et al. | |
| D375,844 S | 11/1996 | Edwards et al. | |
| 5,573,719 A | 11/1996 | Fitting | |
| 5,575,874 A | 11/1996 | Griesbach, III et al. | |
| 5,580,418 A | 12/1996 | Alikhan | |
| 5,599,420 A | 2/1997 | Yeo et al. | |
| 5,607,414 A | 3/1997 | Richards et al. | |
| 5,624,427 A | 4/1997 | Dreier et al. | |
| 5,626,571 A | 5/1997 | Young et al. | |
| 5,628,097 A | 5/1997 | Benson | |
| 5,620,214 A | 7/1997 | Anderson et al. | |
| 5,648,142 A | 7/1997 | Phillips | |
| 5,656,119 A | 8/1997 | Srinivasan et al. | |
| 5,658,639 A | 8/1997 | Curro | |
| 5,667,619 A | 9/1997 | Alikhan | |
| 5,667,625 A | 9/1997 | Alikhan | |
| 5,681,300 A | 10/1997 | Ahr | |
| 5,683,375 A | 11/1997 | Osborn, III et al. | |
| 5,691,035 A | 11/1997 | Chappell et al. | |
| 5,700,255 A | 12/1997 | Curro et al. | |
| 5,704,101 A | 1/1998 | Majors et al. | |
| 5,709,829 A | 1/1998 | Giacometti | |
| 5,714,107 A | 2/1998 | Levy et al. | |
| 5,723,087 A | 3/1998 | Chappell et al. | |
| 5,725,705 A | 3/1998 | Nagahama et al. | |
| 5,730,738 A | 3/1998 | McFall et al. | |
| 5,743,776 A | 4/1998 | Igaue | |
| 5,792,404 A | 8/1998 | Cree et al. | |
| 5,804,021 A | 9/1998 | Abuto et al. | |
| 5,814,389 A | 9/1998 | Giacometti | |
| 5,817,394 A | 10/1998 | Alikhan et al. | |
| 5,817,400 A | 10/1998 | Chen et al. | |
| 5,830,555 A | 11/1998 | Srinivasan | |
| 5,841,107 A | 11/1998 | Riva | |
| 5,858,504 A | 1/1999 | Fitting | |
| 5,876,391 A | 3/1999 | Roe et al. | |
| 5,879,494 A | 3/1999 | Hoff et al. | |
| 5,891,544 A | 4/1999 | Chappell et al. | |
| 5,895,623 A | 4/1999 | Trokhan et al. | |
| 5,914,084 A | 6/1999 | Benson et al. | |
| 5,916,661 A | 6/1999 | Benson | |
| 5,919,177 A | 7/1999 | Georger | |
| 5,925,026 A | 7/1999 | Arteman et al. | |
| 5,932,316 A | 8/1999 | Cree et al. | |

(56) References Cited

U.S. PATENT DOCUMENTS

| | | |
|---|---|---|
| 5,961,505 A | 10/1999 | Coe et al. |
| 5,964,742 A | 10/1999 | McCormack et al. |
| 5,968,029 A | 10/1999 | Chappell |
| 5,986,167 A | 11/1999 | Arteman et al. |
| 5,989,688 A | 11/1999 | Barge |
| 5,993,432 A | 11/1999 | Lodge |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,048,600 A | 4/2000 | Hansson |
| 6,049,024 A | 4/2000 | Thomas |
| 6,057,023 A | 5/2000 | Shimono et al. |
| 6,059,764 A | 5/2000 | Osborn, III et al. |
| 6,096,016 A | 8/2000 | Tsuji et al. |
| 6,103,953 A | 8/2000 | Cree |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,150,002 A | 11/2000 | Varona |
| 6,155,083 A | 12/2000 | Goeser et al. |
| 6,168,849 B1 | 1/2001 | Braverman et al. |
| 6,171,682 B1 | 1/2001 | Raidel |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,290,686 B1 | 9/2001 | Tanzer |
| 6,323,388 B1 | 11/2001 | Melius et al. |
| 6,350,332 B1 | 2/2002 | Thomas |
| 6,362,391 B1 * | 3/2002 | Mizutani ............ A61F 13/51108 604/379 |
| 6,383,431 B1 | 5/2002 | Dobrin et al. |
| 6,395,122 B1 | 5/2002 | Hisanaka et al. |
| 6,395,211 B1 | 5/2002 | Dettmer et al. |
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen |
| 6,451,718 B1 | 9/2002 | Yamada et al. |
| 6,452,064 B1 | 9/2002 | Thoren et al. |
| 6,458,447 B1 | 10/2002 | Cabell |
| 6,479,130 B1 | 11/2002 | Takai et al. |
| D466,702 S | 12/2002 | Carlson et al. |
| 6,491,928 B1 | 12/2002 | Smith, III |
| 6,506,329 B1 | 1/2003 | Curro et al. |
| 6,534,149 B1 * | 3/2003 | Daley .................. A61F 13/512 428/131 |
| 6,537,936 B1 | 3/2003 | Busam et al. |
| 6,545,197 B1 | 4/2003 | Muller et al. |
| 6,605,172 B1 * | 8/2003 | Anderson ............... B29C 55/18 156/199 |
| 6,610,391 B2 | 8/2003 | Molee |
| 6,613,028 B1 | 9/2003 | Daley |
| 6,613,954 B1 | 9/2003 | Horney et al. |
| 6,620,485 B1 | 9/2003 | Benson et al. |
| 6,626,961 B1 | 9/2003 | Everhart et al. |
| 6,632,504 B1 | 10/2003 | Gillespie et al. |
| D481,872 S | 11/2003 | Hennel et al. |
| 6,647,549 B2 | 11/2003 | McDevitt et al. |
| 6,669,878 B2 | 12/2003 | Yamada et al. |
| 6,703,330 B1 * | 3/2004 | Marsh .................. A61F 13/532 442/118 |
| 6,716,498 B2 | 4/2004 | Curro et al. |
| 6,721,987 B2 | 4/2004 | McDevitt et al. |
| 6,726,870 B1 | 4/2004 | Benson et al. |
| 6,730,622 B2 | 5/2004 | Curro et al. |
| 6,740,792 B2 | 5/2004 | Waldroup et al. |
| D494,369 S | 8/2004 | McDevitt et al. |
| 6,794,626 B2 | 9/2004 | Copat et al. |
| 6,808,791 B2 | 10/2004 | Curro et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,855,220 B2 | 2/2005 | Wildeman |
| 6,863,960 B2 | 3/2005 | Curro et al. |
| 6,869,660 B2 | 3/2005 | Wildeman |
| 6,872,274 B2 | 3/2005 | Kauschke et al. |
| 6,878,433 B2 | 4/2005 | Curro et al. |
| 6,884,494 B1 | 4/2005 | Curro et al. |
| 6,911,573 B2 | 6/2005 | Chen et al. |
| 6,955,847 B1 | 10/2005 | Itou et al. |
| 7,005,558 B1 | 2/2006 | Johansson et al. |
| 7,037,569 B2 | 5/2006 | Curro et al. |
| 7,137,971 B2 | 11/2006 | Tanzer |
| 7,154,020 B2 | 12/2006 | Nakashita |
| 7,172,801 B2 | 2/2007 | Hoying et al. |
| 7,976,524 B2 | 7/2011 | Kudo et al. |
| 8,211,815 B2 * | 7/2012 | Baker ............... A61F 13/15707 428/179 |
| 8,936,584 B2 | 1/2015 | Zander et al. |
| 2002/0039867 A1 | 4/2002 | Curro et al. |
| 2002/0040211 A1 | 4/2002 | Drevik |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2002/0177827 A1 | 11/2002 | Noda et al. |
| 2002/0180092 A1 | 12/2002 | Abba et al. |
| 2003/0021951 A1 | 1/2003 | Desai et al. |
| 2003/0028165 A1 | 2/2003 | Curro et al. |
| 2003/0036741 A1 * | 2/2003 | Abba ............... A61F 13/15707 604/385.101 |
| 2003/0050589 A1 | 3/2003 | McDevitt et al. |
| 2003/0077970 A1 | 4/2003 | DeLucia |
| 2003/0085213 A1 | 5/2003 | Burckhardt et al. |
| 2003/0093046 A1 | 5/2003 | Kim et al. |
| 2003/0097113 A1 | 5/2003 | Molee |
| 2003/0124927 A1 | 7/2003 | Waldroup |
| 2003/0191442 A1 | 10/2003 | Bewick-Sonntag |
| 2003/0191443 A1 | 10/2003 | Taylor |
| 2004/0022993 A1 | 2/2004 | Wildeman |
| 2004/0121686 A1 | 6/2004 | Wong et al. |
| 2004/0122396 A1 | 6/2004 | Maldonado et al. |
| 2004/0126531 A1 | 7/2004 | Harvey et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0161991 A1 | 8/2004 | Walton et al. |
| 2004/0229008 A1 | 11/2004 | Hoying |
| 2004/0242097 A1 | 12/2004 | Hasenoehrl et al. |
| 2004/0253894 A1 | 12/2004 | Fell et al. |
| 2004/0265533 A1 | 12/2004 | Hoying |
| 2004/0265534 A1 | 12/2004 | Curro et al. |
| 2005/0004547 A1 * | 1/2005 | Lavash ............. A61F 13/47218 604/385.16 |
| 2005/0017017 A1 | 1/2005 | Crosby et al. |
| 2005/0071938 A1 | 4/2005 | McDevitt et al. |
| 2005/0096614 A1 | 5/2005 | Perez et al. |
| 2005/0118389 A1 | 6/2005 | Wildeman |
| 2005/0123726 A1 | 6/2005 | Broering et al. |
| 2005/0279470 A1 | 12/2005 | Redd et al. |
| 2005/0281978 A1 | 12/2005 | Cabell |
| 2006/0019056 A1 | 1/2006 | Turner et al. |
| 2006/0041239 A1 | 2/2006 | Nagahara et al. |
| 2006/0058761 A1 * | 3/2006 | Kudo .................. A61F 13/4704 604/380 |
| 2006/0058762 A1 * | 3/2006 | Yang ................. A61F 13/15203 604/380 |
| 2006/0069367 A1 | 3/2006 | Waksmundzki |
| 2006/0189954 A1 * | 8/2006 | Kudo ................ A61F 13/15203 604/380 |
| 2006/0206074 A1 | 9/2006 | Bernal et al. |
| 2006/0286343 A1 | 12/2006 | Curro et al. |
| 2007/0116926 A1 | 5/2007 | Hoying et al. |
| 2007/0135787 A1 | 6/2007 | Raidel et al. |
| 2007/0299416 A1 | 12/2007 | Noda et al. |
| 2008/0221538 A1 | 9/2008 | Zhao et al. |
| 2008/0221539 A1 | 9/2008 | Zhao |

(56) References Cited

U.S. PATENT DOCUMENTS

2008/2178091          9/2008  Zhao et al.
2013/0304012 A1      11/2013  Zhao et al.
2020/0353725 A1      11/2020  Mori et al.

FOREIGN PATENT DOCUMENTS

| EP | 0 963 747 A1 | 12/1999 |
| EP | 1 004 412 A1 | 5/2000 |
| EP | 1 217 106 B1 | 6/2002 |
| FR | 2 713 083 A1 | 6/1995 |
| GB | 950 074 | 2/1964 |
| GB | 1 088 991 A | 10/1967 |
| JP | 2002011137 A | 1/2002 |
| WO | WO 93/01780 | 2/1993 |
| WO | 9517147 A1 | 6/1995 |
| WO | WO 95/15138 A1 | 6/1995 |
| WO | WO 97/00656 A1 | 1/1997 |
| WO | WO 01/76523 A1 | 10/2001 |
| WO | WO 02/100632 A1 | 12/2002 |
| WO | WO 2005/011936 A1 | 2/2005 |

OTHER PUBLICATIONS

All Office Actions; U.S. Appl. No. 11/714,020, filed Mar. 5, 2007.
All Office Actions; U.S. Appl. No. 11/714,020, filed Jul. 12, 2013.

\* cited by examiner

DISPOSABLE ABSORBENT ARTICLE

FIELD OF THE INVENTION

The present invention relates to absorbent cores for disposable absorbent articles such as sanitary napkins and disposable diapers.

BACKGROUND OF THE INVENTION

Disposable absorbent articles such as disposable diapers and feminine hygiene articles are well known in the art. Such articles are designed to absorb exudates from the wearer's body. Disposable absorbent articles typically have a fluid permeable body contacting layer called a topsheet, a fluid impermeable layer called a backsheet joined to the topsheet, and an absorbent layer referred to as an absorbent core sandwiched between the topsheet and backsheet. In operation fluid exiting the wearer's body enters the disposable absorbent article through the topsheet and is stored in the absorbent core. The backsheet prevents any excess fluid that is not absorbed from exiting the disposable absorbent article. For disposable absorbent articles like sanitary napkins intended to be worn with other clothing, the backsheet can be a garment-facing layer, and typically aids in preventing soiling of the clothing.

Other elements can be included in disposable absorbent articles, including additional absorbent layers having structures designed for certain functions. For example, a secondary topsheet can be an absorbent layer placed between the topsheet and the absorbent core, and having a structure designed to wick fluid quickly away from the topsheet and into the absorbent core. Likewise, multiple layers of absorbent cores can be used, each layer having fluid handling properties designed to securely move fluid into the absorbent core for secure storage. Additionally, each layer of absorbent core material can itself be a layered or laminate structure having discrete layers as is known in the art of air laying webs using multiple air laying heads or beams. In a layered absorbent core material, any one discrete layer can comprise a different type or blend of fibers with respect to one other discrete layer.

It is known to design absorbent cores having a structure such that fluid movement from the topsheet toward the backsheet, i.e., away from the wearer's body, is facilitated. For example, fibrous layered absorbent cores in which the capillarity of the fibrous layers is increased with each layer are known. Likewise, it is known to have layered absorbent cores wherein with each succeeding layer in a direction away from the topsheet the permeability is decreased. In this manner, fluid entering through the topsheet first encounters a layer having high permeability and low capillarity to facilitate quick fluid uptake. From this first layer, the fluid can encounter a layer having less permeability and higher capillarity, such that the fluid continues to move away from the topsheet, but at a slower rate. This is generally acceptable because once the fluid is away from the wearer's body the rate at which it moves to other portions of the absorbent core is not critical.

In known absorbent cores there is a well-known tradeoff between the permeability of a material and its capillarity. In general, known materials that are relatively higher in permeability are relatively lower in capillarity, and vice versa. For disposable absorbent articles, in which it is desirable to have both parameters uncoupled, a positive change in one of these parameters results in a corresponding negative change in the other. Because permeability directly affects a material's acquisition rate and capillarity directly impacts the movement of fluid due to limits in capillary pressure, this tradeoff in properties has, in the past, resulted in an absorbent core chosen for a balance of properties. The necessary tradeoff, however, has resulted in absorbent structures, including absorbent cores, in which the desired levels of acquisition rate and effective fluid movement to secure storage cannot be achieved simultaneously.

Accordingly, it would be desirable to have an absorbent article and an absorbent core material in which both permeability and capillarity pressure can be maintained at desirable levels simultaneously in an absorbent core.

Additionally, it would be desirable to have an absorbent article and an absorbent core material in which the negative aspects of either of permeability or capillarity pressure when one or the other is more optimized, are minimized.

Further, it would be desirable to have an absorbent article and an absorbent material in which the tradeoff between permeability and capillarity pressure is managed such that delivering relatively higher permeability can be accomplished without a decrease in capillarity pressure.

SUMMARY OF THE INVENTION

An absorbent article that can be a sanitary napkin is disclosed. The absorbent article comprises a topsheet joined to a backsheet and has an absorbent core material disposed therebetween, the absorbent core material being a fibrous absorbent material exhibiting on one side thereof discrete raised portions. The raised portions define a continuous network of channels, the channels defining a void region adjacent the topsheet of the sanitary napkin, at least one of the discrete raised portions has a density of about 0.07 g/cc to 0.12 g/cc and at least one channel has a density between 0.199 g/cc and 0.226 g/cc.

A sanitary napkin is disclosed. The sanitary napkin having in layered order a topsheet, a secondary topsheet, an absorbent core, and a backsheet. The topsheet and backsheet being joined. The secondary topsheet is an absorbent fibrous web having discrete regions of distinct fiber disruption relative to adjacent regions. The absorbent core material is an absorbent fibrous material exhibiting on one side thereof discrete raised portions. The raised portions defining a continuous network of channels. The channels defining a void region adjacent said secondary topsheet. At least one of the discrete raised portions has a density of about 0.07 g/cc to 0.12 g/cc and at least one channel has a density between 0.199 g/cc and 0.226 g/cc.

An absorbent article is disclosed. The absorbent article having in layered order a topsheet, a secondary topsheet, an absorbent core, and a backsheet. The topsheet and said backsheet being joined. The layers being in a generally flat, layered relationship. The secondary topsheet being an absorbent airlaid fibrous web comprising cellulosic fibers. The secondary topsheet having discrete regions of distinct fiber disruption relative to adjacent regions. The absorbent core material is an airlaid absorbent fibrous material comprising cellulosic fibers and exhibiting on one side thereof discrete raised portions. The raised portions being oriented toward said secondary topsheet and defining a continuous network of channels. The channels defining a void region adjacent said secondary topsheet of said absorbent article. At least one of the discrete raised portions has a density of about 0.07 g/cc to 0.12 g/cc and at least one channel has a density between 0.199 g/cc and 0.226 g/cc.

DETAILED DESCRIPTION OF THE INVENTION

One embodiment of the invention is an absorbent core having utility as the fluid storage component of a disposable absorbent article, such as a feminine hygiene article. One embodiment of a feminine hygiene article of the present invention, a sanitary napkin 10, is shown in perspective view in FIG. 1. While the invention is disclosed in FIG. 1 as an embodiment of a sanitary napkin 10, the disclosed features of the invention can also be useful when incorporated in other feminine hygiene articles, such as incontinence pads and pantiliners. Therefore, the description below is in the context of a sanitary napkin, but it is applicable to feminine hygiene articles in general. Likewise, the absorbent core of the present invention can find utility in other disposable absorbent articles, including disposable diapers, adult incontinent devices, hemorrhoid treatment pads, bandages, and the like. Still further, the structure produced by the methods and apparatus disclosed herein can find utility in other webs for which surface texture of heterogeneous fiber structure is beneficial, such as wipes, scouring pads, dry-mop pads (such as SWIFFER® pads), and the like.

Figure 1:
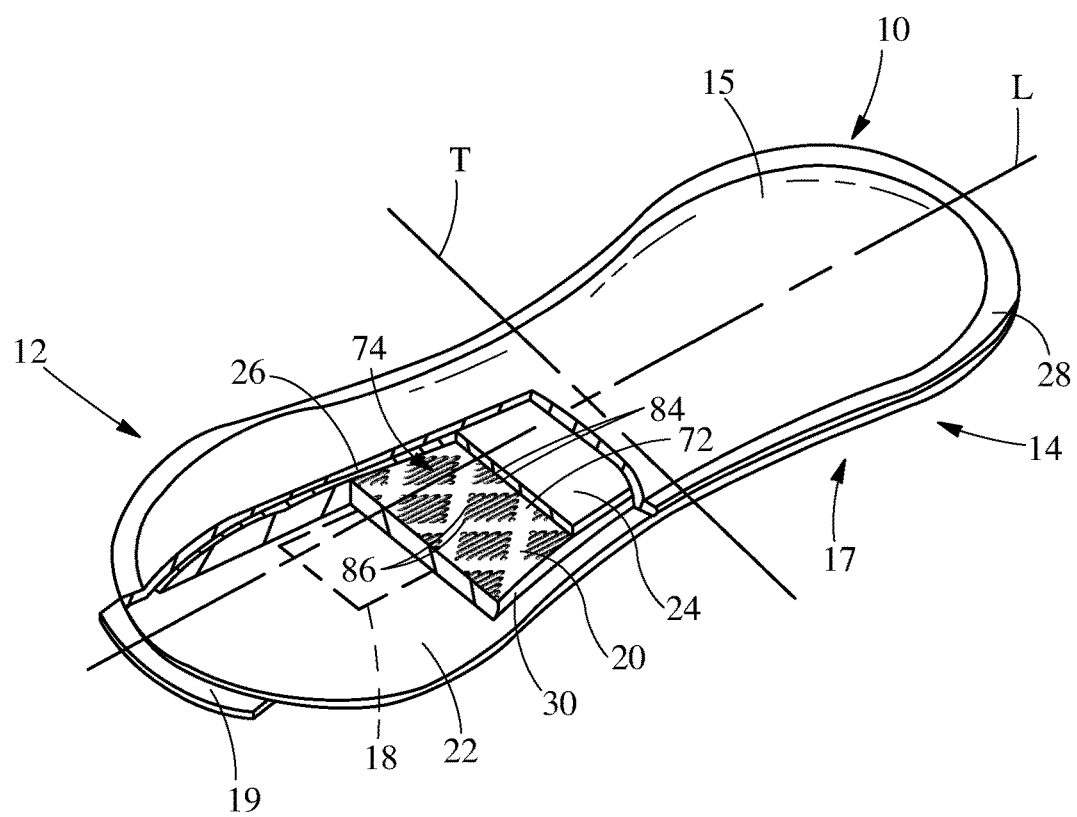
FIG. 1 is a partial cut-away perspective view of a sanitary napkin embodying the present invention.

Sanitary napkin 10 can be considered in three regions, two end regions 12 and 14 each comprising about one-third of the overall length, and a middle region 16. Sanitary napkin 10 has a body-facing surface (or side) 15 that is in contact with the user's body during use and a garment-facing surface (or side) 17 that is in contact with the user's undergarment during use. In general, each component layer of the sanitary napkin 10 can be said to have a body-facing side and a garment-facing side, the sides being determined by their orientation relative to the in-use orientation of the article. Sanitary napkin 10 has a longitudinal centerline L and a transverse centerline T, the centerlines being perpendicular to one another in the plane of the sanitary napkin when in a flat out configuration, as shown in FIG. 1. In one embodiment the sanitary napkin can be generally symmetric about both centerlines, while in other embodiments the sanitary napkin can be generally asymmetric about either centerline. In the embodiment shown in FIG. 1, sanitary napkin 10 is symmetric about the longitudinal centerline L and symmetric about transverse centerline T. Feminine hygiene articles can also be provided with lateral extensions known in the art as "flaps" or "wings" (not shown in FIG. 1) intended to fold over and cover the panty elastics in the crotch region of the user's undergarment.

Sanitary napkin 10 can have any shape known in the art for feminine hygiene articles, including generally symmetric "hourglass" shaped as shown in FIG. 1, or tapering inwardly from a relatively greater transverse width in a portion of one of the end regions to a relatively smaller transverse width at the middle region, such that the maximum transverse width of one end, e.g., end region 12, of the pad is greater than the maximum transverse width of the other end, e.g., end region 14. Transverse width is defined herein as the edge-to-edge dimension across the article, measured parallel to the transverse centerline T. Such pads can be described as pear shaped, bicycle-seat shaped, trapezoidal shaped, wedge shaped, or otherwise described in a manner that connotes a two-dimensional shape having two ends in which one end is larger than the other in a maximum width dimension.

Sanitary napkin 10 can have an absorbent core 20 to absorb and store bodily fluids discharged during use. In some embodiments of sanitary napkins, pantiliners, incontinence pads, or other such devices of the present invention, an absorbent core is not necessary, the pad consisting only of a topsheet (that can have some absorbency) and a fluid impermeable backsheet. Absorbent core 20 can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

In one embodiment absorbent core 20 can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 0.25 psi. The absorbent core can comprise absorbent gelling materials (AGM), including AGM fibers, as is known in the art.

Absorbent core 20 can be formed or cut to a shape, the outer edges of which define a core periphery 30. The shape of absorbent core 20 can be generally rectangular, circular, oval, elliptical, or the like. Absorbent core 20 can be generally centered with respect to the longitudinal centerline L and transverse centerline T. The profile of absorbent core 20 can be such that more absorbent is disposed near the center of the absorbent article. For example, the absorbent core can be thicker in the middle, and tapered at the edges in a variety of ways known in the art.

Absorbent core 20 can be an airlaid core of the type disclosed in U.S. Pat. No. 5,445,777; or U.S. Pat. No. 5,607,414. Absorbent core can comprise a high capacity and highly absorbent core material of the type generally referred to as HIPE foams, such as those disclosed in U.S. Pat. No. 5,550,167; 5,387,207; 5,352,711; and 5,331,015. In one embodiment, the absorbent core can have a capacity after desorption at 30 cm of less than about 10% of its free absorbent capacity; a capillary absorption pressure of from about 3 to about 20 cm; a capillary desorption pressure of from about 8 to about 25 cm; a resistance to compression deflection of from about 5 to about 85% when measured under a confining pressure of 0.74 psi; and a free absorbent capacity of from about 4 to 125 grams/gram. Each of these parameters can be determined as set forth in U.S. Pat. No. 5,550,167, issued Aug. 27, 1996 to DesMarais. One advantage of utilizing the airlaid or HIPE foam cores as disclosed is that the absorbent core can be made very thin. For example, an absorbent core of the present invention can have an average caliper (thickness) of less than about 3 mm, or less than about 2 mm, and the thickness can be less than about 1 mm.

To prevent absorbed bodily exudates from contacting the wearer's garments, sanitary napkin 10 can have a liquid impermeable backsheet 22. Backsheet 22 can comprise any of the materials known in the art for backsheets, such as polymer films and film/nonwoven laminates. To provide a degree of softness and vapor permeability for the garment-facing side of sanitary napkin 10, backsheet 22 can be a vapor permeable outer layer on the garment-facing side of the sanitary napkin 20. The backsheet 22 can be formed from any vapor permeable material known in the art. Backsheet 22 can comprise a microporous film, an apertured formed film, or other polymer film that is vapor permeable, or rendered to be vapor permeable, as is known in the art. One suitable material is a soft, smooth, compliant, vapor pervious material, such as a nonwoven web that is hydrophobic or rendered hydrophobic to be substantially liquid impermeable. A nonwoven web provides for softness and conformability for comfort, and can be low noise producing so that movement does not cause unwanted sound.

To provide for softness next to the body, sanitary napkin 10 can have a body-facing layer, referred to herein as topsheet 26. Topsheet 26 can be formed from any soft, smooth, compliant, porous material which is comfortable against human skin and through which fluids such as urine or vaginal discharges can pass. Topsheet 26 can comprise fibrous nonwoven webs and can comprise fibers as are known in the art, including bicomponent and/or shaped fibers. Bicomponent fibers can comprise polypropylene (PP) and polyethylene (PE) in known configurations, including core/sheath, side by side, islands in the sea, or pie. Shaped fibers can be tri-lobal, H-shaped in cross section, or any other known cross-sectional shape. Topsheet 26 can also be a liquid permeable polymer film, such as an apertured film, or an apertured formed film as is known on sanitary napkins such as ALWAYS® brand sanitary napkins.

At least one, and preferably both, of topsheet 26 and backsheet 22 define a shape, the edge of which defines an outer periphery 28 of the sanitary napkin 10. In one embodiment, both topsheet 26 and backsheet 22 define the sanitary napkin 10 outer periphery 28. The two layers can be die cut, as is known in the art, for example, after combining all the components into the structure of the sanitary napkin 10 as described herein. However, the shape of either topsheet 26 or backsheet 22 can be independently defined.

Disposable absorbent articles can include a lotion, skin care ingredients, fragrances, odor control agents, and other components. In one embodiment, a lotion that can include a skin care composition can be added by spraying, extrusion or slot coating to a topsheet. The skin care composition can be hydrophilic or hydrophobic, and can have from about 0.001% to about 0.1% by weight of hexamidine, from about 0.001% to about 10% by weight of zinc oxide, from about 0.01% to about 10% by weight of niacinamide, and a carrier such as petrolatum. The lotion can include glycols, including poly propylene glycol, either in a compound or neat. Lotions and skin care agents can be those described in co-owned and co-pending U.S. Ser. No. 10/152,924, filed on May 21, 2002, U.S. Ser. No. 09/968,154, and U.S. Ser. No. 10/152,924, filed on May 21, 2002.

Interposed between the absorbent core 20 and topsheet 26 can be at least one fluid permeable secondary topsheet 24. Secondary topsheet 24 can aid in rapid acquisition and/or distribution of fluid and is preferably in fluid communication with the absorbent core 20. In one embodiment, the secondary topsheet 24 does not completely cover the absorbent core 20, but it can extend laterally to core periphery 30. In one embodiment, topsheet, secondary topsheet, or the absorbent core can be layered structures, the layers facilitating fluid transport by differences in fluid transport properties, such as capillary pressure.

Each web of absorbent core material can itself be a layered structure having discrete layers as is known in the art of air laying webs using multiple air laying heads or beams. In a layered absorbent core material, any one discrete layer can comprise a different type or blend of fibers with respect to one other discrete layer.

In one embodiment, absorbent core 20 does not extend laterally outward to the same extent as either topsheet 26 or backsheet 22, but the sanitary napkin 10 outer periphery 28 can be substantially larger than the core outer periphery 30. In this manner, the region of sanitary napkin 10 between the core periphery 30 and the sanitary napkin 10 outer periphery 28 can define a breathable zone that permits vapors to go through portions of the sanitary napkin, thereby escaping and providing for dryer comfort when worn. A sanitary napkin having a breathable zone can be according to the teachings of U.S. Ser. No. 10/790,418, filed Mar. 1, 2004.

All the components can be adhered together by means well known in the art with adhesives, including hot melt adhesives, as is known in the art. The adhesive can be Findlay H2128 UN or Savare PM 17 and can be applied using a Dynafiber HTW system.

As is typical for sanitary napkins and the like, the sanitary napkin 10 of the present invention can have panty fastening adhesive 18 disposed on the garment-facing side 17 of backsheet 22. Panty fastening adhesive 18 can be any of known adhesives used in the art for this purpose, and can be covered prior to use by a release paper 19, as is well known in the art. If flaps or wings are present, panty fastening adhesive can be applied to the garment facing side so as to contact and adhere to the underside of the wearer's panties.

The above disclosure is meant to give a general description of the basic parts of feminine hygiene articles such as sanitary napkins and the like as they are known in the art. The description is not intended to be limiting. Any and all of various known elements, features and processes of known sanitary napkins, pantiliners, sanitary napkins, and the like can be incorporated in the feminine hygiene article of the present invention as desired or needed for commercial manufacture, or for particular use benefits. For example, sanitary napkins can be according to the disclosure of U.S. Pat. No. 4,950,264 issued to Osborn III Aug. 21, 1990, and an incontinence pad can be according to the disclosure of U.S. Pat. No. 5,439,458 issued to Noel et al. Aug. 8, 1995.

The present invention utilizes absorbent materials that for sanitary napkins can include a secondary topsheet and/or an absorbent core that have been modified from an as-made state to exhibit higher permeability without a corresponding decrease in capillary pressure, such that the secondary topsheet and/or core of the present invention provides for faster acquisition rates and greater retained capacity relative to the unmodified material, and with respect to known materials. These desirable properties can be imparted to known fibrous web materials by forming them by one or more of known formation means, such as by known methods for making extruded nonwoven webs and airlaid fibrous webs. Without being bound by theory, it is believed that the modifications disclosed herein produce modifications of the base web in the form of relatively small, localized, discrete regions of increased permeability, which together with the substantially unmodified regions, produce an average, or "macro" effect of a web in which the either the permeability or capillary pressure can be improved without the expected negative impact on the other.

In one aspect, known absorbent web materials in an as-made can be considered as being homogeneous throughout. Being homogeneous, the fluid handling properties of the absorbent web material are not location dependent, but are substantially uniform at any area of the web. Homogeneity can be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling properties of the web material are location dependent. Therefore, for the heterogeneous absorbent materials of the present invention, at discrete locations the density or basis weight of the web is substantially different than the average density or basis weight for the web. The heterogeneous nature of the absorbent web of the present invention permits the negative aspects of either of permeability or capillarity pressure to be minimized by rendering discrete portions highly permeable and other discrete portions to have high capillarity. Likewise, the tradeoff between permeability and capillary pressure is managed such that delivering relatively higher permeability can be accomplished without a decrease in capillarity pressure. The heterogeneous web of the present invention appears to uncouple the permeability/capillarity pressure tradeoff. The formation means and the absorbent core materials made thereby are described below.

Four formation means known for deforming a generally planar fibrous web into a three-dimensional structure are utilized in the present invention to modify as-made absorbent materials into absorbent materials having relatively higher permeability without a significant corresponding decrease in capillary pressure. Each of the four formation means disclosed herein are disclosed as comprising a pair of inter-meshing rolls, typically steel rolls having inter-engaging ridges or teeth and grooves. However, it is contemplated that other means for achieving formation can be utilized, such as the deforming roller and cord arrangement disclosed in US 2005/0140057 published Jun. 30, 2005. Therefore, all disclosure of a pair of rolls herein is considered equivalent to a roll and cord, and a claimed arrangement reciting two inter-meshing rolls is considered equivalent to an inter-meshing roll and cord where a cord functions as the ridges of a mating inter-engaging roll. In one embodiment, the pair of intermeshing rolls of the instant invention can be considered as equivalent to a roll and an inter-meshing element, wherein the inter-meshing element can be another roll, a cord, a plurality of cords, a belt, a pliable web, or straps. Likewise, while the disclosure of four formation means is illustrated herein, other known formation technologies, such as creping, necking/consolidation, corrugating, embossing, button break, hot pin punching, and the like are believed to be able to produce absorbent materials having some degree of relatively higher permeability without a significant corresponding decrease in capillary pressure.

Figure 2:
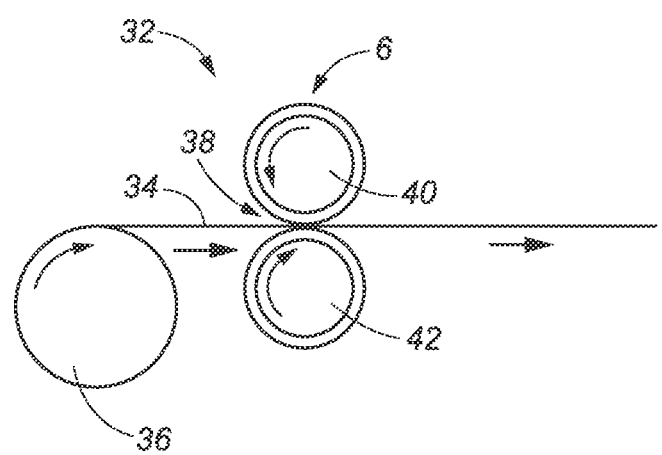
FIG. 2 is a schematic representation of a process for mechanical modification of web materials through a nip of a pair of inter-meshing rolls.

The first formation means useful in the present invention is a process commonly referred to as "ring rolling". Referring to the drawings, and particularly to FIG. 2 thereof, there is schematically illustrated at 32 apparatus and a method for modifying the physical and performance properties of a web by the process commonly referred to as ring rolling, for example, a nonwoven web 34 that is carried on and that is drawn from a supply roll 36. For absorbent core materials, such as air laid nonwoven webs, the ring rolling apparatus and method can produce a physically modified web having improved fluid handling properties and modified dimensions that may serve to improve both the performance and the fit of disposable articles that incorporate such modified materials. Additionally, after being modified in the disclosed apparatus and after having acquired the desired physical properties hereinafter described, such modified nonwoven webs are capable of further processing, if desired, whether alone or together with other materials, and without the modified nonwoven web experiencing disintegration, rupture, or loss of integrity.

Referring again to FIG. 2, nonwoven web 34 is withdrawn from supply roll 36 and travels in the direction indicated by the arrow. Nonwoven web 34 is fed to the nip 38 formed by a pair of opposed forming rolls 40 and 42 that together define a first forming station 6. The structure and relative positions of forming rolls 40 and 42 of first forming station 50 are shown in an enlarged perspective view in FIG. 3. As shown, rolls 40 and 42 are carried on respective rotatable shafts 44, 46, having their axes of rotation disposed in parallel relationship. Each of rolls 40 and 42 includes a plurality of axially-spaced, side-by-side, circumferentially-extending, equally-configured ridges 52 that can be in the form of thin fins of substantially rectangular cross section, or they can have a triangular or an inverted V-shape when viewed in cross section. If they are triangular, the vertices of ridges 52 are outermost with respect to the surface of rolls 40 and 42. In any configuration, the outermost tips of the teeth are preferably rounded, as shown in greater detail in FIGS. 4 and 5, to avoid cuts or tears in the materials, such as nonwoven web 34, that pass between the rolls.

The spaces between adjacent ridges 52 define recessed, circumferentially-extending, equally configured grooves 54. The grooves 54 can be of substantially rectangular cross section when the teeth are of substantially rectangular cross section, and they can be of inverted triangular cross section when the teeth are of triangular cross section. Thus, each of forming rolls 40 and 42 includes a plurality of spaced ridges 52 and alternating grooves 54 between each pair of adjacent teeth. The teeth and the grooves need not each be of the same width, however, and preferably the grooves have a larger width than that of the teeth, to permit the material that passes between the interengaged rolls to be received within the respective grooves and to be locally stretched, as will be explained hereinafter.

Figure 4:
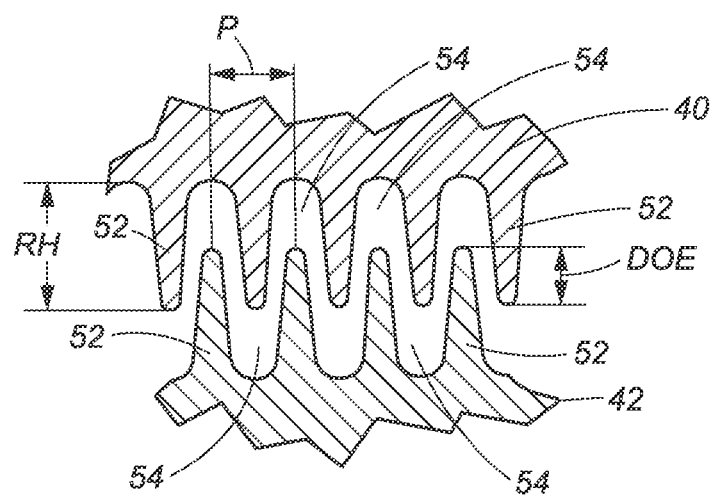
FIG. 4 is an enlarged, fragmentary, cross-sectional view showing the interengagement of teeth and grooves of respective rolls of a ring-rolling apparatus as shown in FIG. 3.

FIG. 4 is an enlarged, fragmentary, cross-sectional view showing the interengagement of ridges 52 and grooves 54 of the respective rolls. Ridges 52 have a tooth height TH and are spaced apart from one another by a preferably uniform distance to define a tooth pitch P. As shown, ridges 52 of one roll extend partially into grooves 54 of the opposed roll to define a "depth of engagement", E, as shown in FIG. 4. The respective axes of rotation of rolls 40 and 42 are spaced from each other such that there is a predetermined space or gap between the opposed sidewalls of the interengaged teeth and grooves of the respective rolls. Also shown is the tooth angle TA, which is the angle formed by adjacent teeth.

Figure 5:
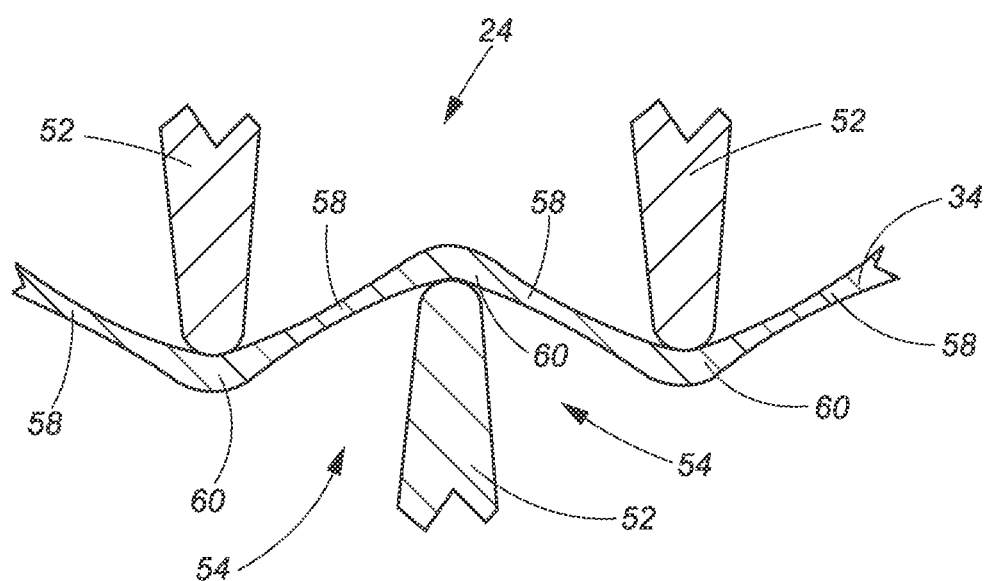
FIG. 5 is an even further enlarged view of a ring-rolling apparatus as shown in FIG. 3 showing several interengaged teeth and grooves with a web of material therebetween.

FIG. 5 is an even further enlarged view of several interengaged ridges 52 and grooves 24 with a web 25 of material therebetween. As shown, a portion of a web, which can be nonwoven web 34 as shown in FIG. 1, is received between the interengaged teeth and grooves of the respective rolls. The interengagement of the teeth and grooves of the rolls causes laterally spaced portions of web 34 to be pressed by ridges 52 into opposed grooves 54. In the course of passing between the forming rolls, the forces of ridges 52 pressing web 34 into opposed grooves 54 impose within web 34 tensile stresses that act in the cross-web direction. The tensile stresses can cause intermediate web sections 58 that lie between and that span the spaces between the tips of adjacent ridges 52 to stretch or extend in a cross-web direction, which can result in a localized reduction of the web thickness at each of intermediate web sections 58. For nonwoven webs, including airlaid webs, the stretching can cause fiber reorientation, a reduction in basis weight, and or controlled fiber destruction in the intermediate web sections 58.

Although the portions of web 34 that lie between the adjacent ridges are locally stretched, the portions of the web that are in contact the tips of the ridges may not undergo a similar degree of extension. Because of the frictional forces that exist between the surfaces at the rounded outer ends of ridges 52 and the adjacent areas 60 of web 34 that are in contact with the ridge surfaces at the outer ends of the ridges, sliding movement of those portions of the web surfaces relative to the ridge surfaces at the outer ends of the ridges is minimized Consequently, in some cases, the properties of the web 34 at those areas of the web that are in contact with the surfaces of the ridge tips changes only slightly, as compared with the web property changes that occur at intermediate web sections 58.

Because of the localized cross-web stretching of web 34 that has taken place, with the consequent increase in web width, the web material that exits from the forming rolls can have a lower basis weight than that of the entering web material, provided the exiting material remains in a substantially flat, laterally extended state. The laterally-stretched web as it exits from between the forming rolls may contract laterally to its original width, in that the web is placed under some tension in the web movement direction, in which case the exiting, modified web may have the same basis weight as it had in its entering condition. If, however, the exiting web is subjected to a sufficiently high web machine direction tension, the exiting web can be made to contract to a smaller width than its original width, in which case the web will have a greater basis weight than its original basis weight. On the other hand, if the web is subjected to sufficient additional cross-web stretching by passing the modified web between so-called Mount Hope rolls, tentering frames, angled idlers, angles nips, or the like as described above, the exiting, modified web can have less than its original basis weight. Thus, by selecting a suitable forming roll tooth and groove configuration, by selecting a suitable web movement direction tension level, and by selecting whether or not to subject the web to additional cross-web stretching, the resulting modified nonwoven web can have a web width that can range from about 25% to about 300% of the initial web width and a basis weight that is less than, equal to, or greater than the web's original basis weight.

Ridges 52 can be generally triangular in cross section having generally rounded ridge tips, as shown in FIGS. 4 and 5, and preferably each of ridges 52 is of the same size so that each of the opposed ridges and grooves on respective forming rolls 40 and 42 interengage with each other along the entire axial lengths of each of the rolls. As shown ridges 66 have a ridge height RH (note that RH can also be applied to groove depth; in one embodiment tooth height and groove depth can be equal), and a ridge-to-ridge spacing referred to as the pitch P. The depth of engagement E, ridge height RH, and pitch P can be varied as desired depending on the properties of the nonwoven webs being processed and the desired characteristics of the processed webs. For example, in general, the greater the level of engagement E, the greater the necessary elongation or fiber-to-fiber mobility characteristics the fibers of the processed web must possess.

By way of example, and not by way of limitation, ridges having a peak-to-peak pitch P of the order of about 0.150 inches, having sidewalls disposed at an included angle of the order of about 12° and having a uniformly rounded ridge tip radius, and having a tip-to-base ridge height RH (and groove depth) of the order of about 0.300 inches can be employed in carrying out the present invention. As will be appreciated by those skilled in the art, the sizes of the respective ridges and grooves can be varied within a wide range and would still be effective to carry out the present invention. In that regard, additional structural details of suitable forming rolls are provided in U.S. Pat. No. 5,156,793, entitled "Method for Incrementally Stretching Zero Strain Stretch Laminate Sheet in a Non-Uniform Manner to Impart a Varying Degree of Elasticity Thereto," which issued on Oct. 20, 1992, to Kenneth B. Buell et al.; in U.S. Pat. No. 5,167,897 entitled "Method for Incrementally Stretching a Zero Strain Stretch Laminate Sheet to Impart Elasticity Thereto," which issued on Dec. 1, 1992, to Gerald M. Sheeter et al.; and in U.S. Pat. No. 5,518,801, entitled "Sheet Materials Exhibiting Elastic-Like Behavior," which issued on May 21, 1996, to Charles W. Chappell et al.

The second means for deforming a web of the present invention is a process commonly referred to as a "SELF" or "SELF'ing" process, in which SELF stands for Structural Elastic Like Film. While the process was originally developed for deforming polymer film to have beneficial structural characteristics, it has been found that the SELF'ing process can be used to produce beneficial structures in nonwoven webs useful as absorbent core materials, including air laid absorbent cores, as disclosed herein.

Figure 6:
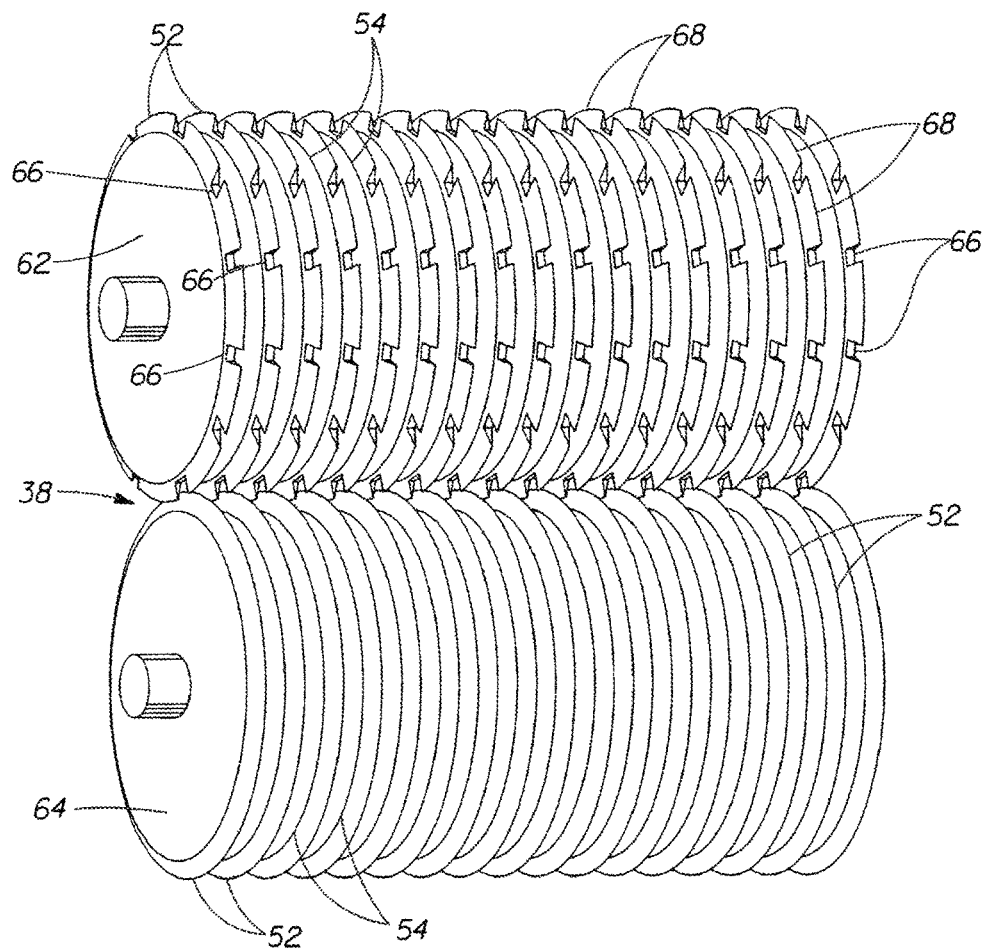
FIG. 6 is schematic representation of a pair of inter-meshing rolls of a process commonly referred to a SELF process.
Figure 7:
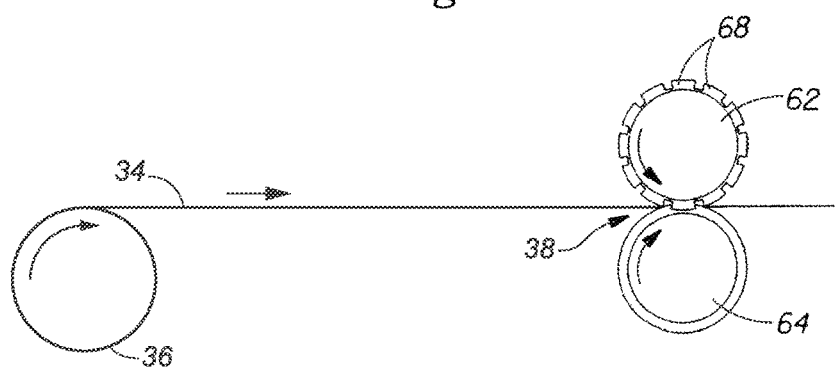
FIG. 7 is a schematic representation of a process for modifying a web by the SELF process.

Referring to FIG. 6, there is shown a configuration of opposed forming rolls for use in a SELF process that can be employed to expand portions of a nonwoven web in the web thickness dimension, by expanding portions of the web out of the X-Y plane in the Z-direction. As shown in FIG. 7, an unmodified nonwoven web 34 can be fed from a supply roll 36 into the nip 38 of opposed forming rolls 62 and 64. Roll 64 includes a plurality of circumferentially-extending, axially-spaced circumferential ridges 52 and grooves 54 similar to those described with respect to the rolls 40 and 42 above. Roll 62 includes a plurality of circumferentially-extending, axially-spaced circumferential ridges 52 wherein portions of the circumferential ridges 52 of roll 62 have been removed to form notches 66 that define a plurality of circumferentially-spaced teeth 68. As shown in FIG. 6, notches 66 on respective axially adjacent circumferential ridges 52 can be aligned laterally to define a plurality of circumferentially-spaced groups of notched regions about the periphery of roll 62. The respective laterally-extending groups of notched regions each extend parallel to the axis of roll 62. Teeth 68 can have a tooth height TH corresponding to ridge height RH, and a tooth pitch corresponding to the ridge pitch P.

As web 34 passes through nip 38, the teeth 68 of roll 62 press a portion of web 34 out of plane to cause permanent, localized Z-direction deformation of web 34. But the portion of the web 34 that passes between the notched regions 66 of roll 62 and the teeth 68 of roll 62 will be substantially unformed in the Z-direction, i.e., the nonwoven web will not be deformed or stretched in that area to the same degree as that of the toothed regions, and can remain substantially planar, while the portions of the web passing between toothed regions of roll 62 and the ridges 52 of roll 64 can be deformed or stretched beyond the elastic limit of the nonwoven, resulting in a plurality of deformed, raised, rib-like elements.

Figure 8:
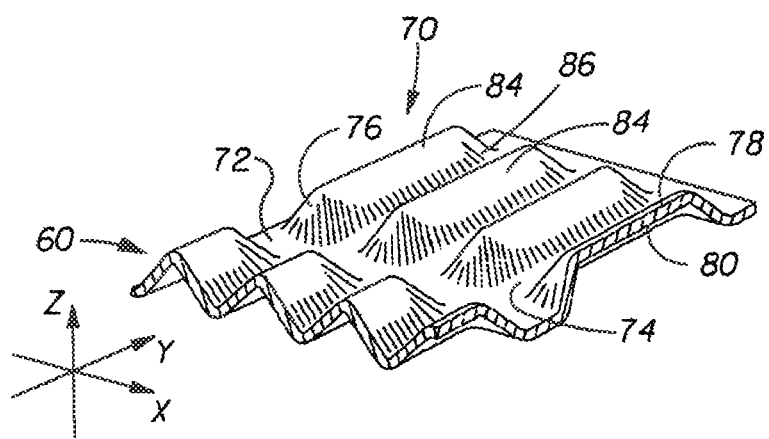
FIG. 8 is a schematic representation of a web after it has passed between a pair of inter-meshing SELF rolls.

Referring now to FIG. 8, there is shown a schematic representation of a portion of a SELF'ed nonwoven web 70 after it has passed between a pair of opposed, interengaged forming rolls 62 and 64 of a SELF process, the rolls having the tooth configurations similar to that shown in FIG. 6. SELF'ed nonwoven web 70 includes a network of distinct regions. The network includes at least a first region 72, a second region 74, and a transitional region 76, which is at the interface between the first region 72 and the second region 74. SELF'ed nonwoven web 70 also has a first surface 78 and an oppositely-facing second surface 80. In the embodiment shown in FIG. 8, SELF'ed nonwoven web 70 includes a plurality of substantially flat, spaced first regions 72 and a plurality of alternating rib-like elements 84. In the preferred embodiment of FIG. 8, the first regions 72 and the second regions 74 are substantially linear, each extending continuously in a direction substantially parallel to the longitudinal axis of the web.

In the embodiment shown in FIG. 8 first regions 72 are substantially planar. That is, the material within first regions 72 is substantially flat and is in substantially the same condition after the modification step undergone by nonwoven web 60 by passage between interengaged rolls 62 and 64 shown in FIG. 6 as it was in before the web 34 was passed between the forming rolls.

In an air laid absorbent core, it has been found that the rib-like elements 84 can beneficially be adjacent to one another and can be separated from each other by an unformed first region 72 which can include the valleys 86 separating adjacent rib-like elements 84. Unformed first region 72 can be areas that have substantially the same material properties as the homogeneous air laid absorbent core before SELF'ing, and can have a width of less than about 0.10 inches measured perpendicular to the x-axis as shown in FIG. 8. The dimensions of the rib-like elements can also be varied, if desired. The rib-like elements protruding in the Z-direction with respect to the plane of the web are raised portions that increase the bulk or caliper of the web, without necessarily increasing the basis weight thereof. The raised portions also define a continuous network of channels in the unformed first regions 72, which channels define a void region between the surface of the web and any adjacent webs when the web is combined into a layered absorbent core for a disposable absorbent product, for example. In one embodiment, the continuous network of channels can define a void region adjacent the topsheet. The void regions can serve to provide void volume in an absorbent core, such that the absorbent core has greater permeability, and can handle "gushes" of fluid more effectively. An interconnected continuous network of channels has channels running in both the MD and the CD directions in the plane of the absorbent core. Channels can facilitate lateral "run off" of fluid such that fluid can more effectively be distributed across the length and width of an absorbent core as well.

In one embodiment, the nonwoven web processed by the SELF process described herein can be a web having absorbency characteristics suitable for use as an absorbent core in a disposable absorbent article. In one embodiment, the web can be an airlaid web of fibers, including cellulosic fibers, synthetic fibers, and blends and combinations thereof. In one embodiment, the airlaid web can be a layered airlaid web, formed of layers in which each layer can differ from an adjacent layer in fiber type, density, basis weight, or combinations thereof. In one embodiment an absorbent core material having rib-like elements formed therein can be used in a layered relationship with a topsheet, wherein the rib-like elements are oriented toward, and are in a contacting relationship with, the topsheet. In one embodiment an absorbent core material having rib-like elements formed therein can be used in a layered relationship with a secondary topsheet, wherein the rib-like elements are oriented toward, and are in a contacting relationship with, the secondary topsheet. A secondary topsheet can be what is commonly referred to as a distribution layer, which can be an absorbent material having fluid handling properties suitable for rapidly distributing fluid in a lateral direction. Alternatively, in another embodiment, the rib-like elements can be used in a layered relationship with a topsheet or secondary topsheet, wherein the rib-like elements are oriented away from, and are not in a contacting relationship with, the topsheet or secondary topsheet.

Figure 10:
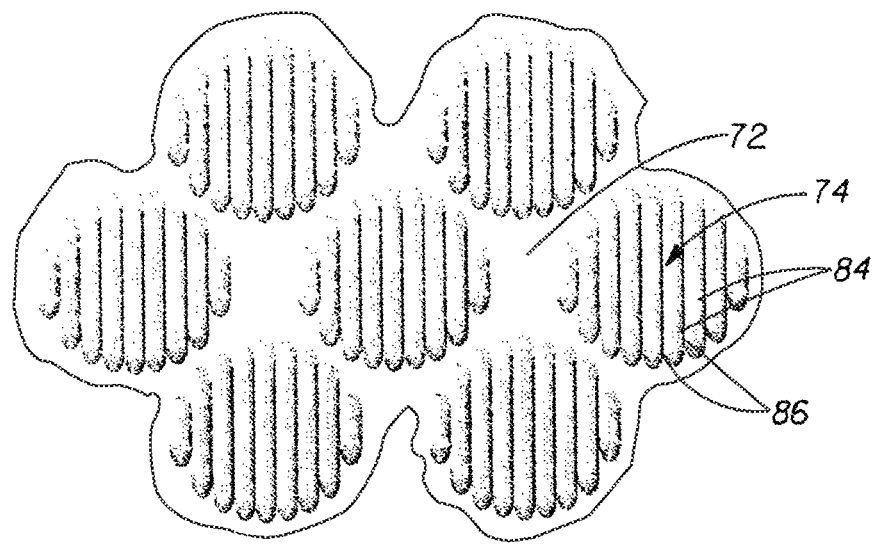
FIG. 10 is a pattern that can be produced in an absorbent material by passing the material between a pair of inter-meshing SELF rolls.

In addition to the surface pattern illustrated in FIG. 8 in the form of rib-like elements each having substantially equal lengths and arranged in rows to define generally rectangular areas of deformation separated by linear first regions 72, the desired formation of a nonwoven web can, if desired, be effected by other forming roll tooth and groove configurations that can cause localized stretching and/or deformation of the nonwoven material. For example, as shown in FIG. 10, instead of spaced rectangular arrays of rib-like elements the deformation pattern can be in the form of rib-like elements defining an array of spaced, diamond-shaped second regions 74 with intervening undeformed first regions 72. Each such diamond-shaped second region 74 is defined by alternating rib-like elements 84 and intervening valleys 86. Examples of methods and apparatus for formation of such diamond-shaped elements are disclosed in U.S. Pat. No. 5,650,214, entitled, "Sheet Materials Exhibiting Elastic-Like Behavior and Soft, Cloth-Like Texture", which issued on Jul. 22, 1997, to Barry J. Anderson, et al., and U.S. Pat. No. 6,383,431, entitled, "Method of Modifying a Nonwoven Fibrous Web For Use as a Component of a Disposable Absorbent Article," which issued May 7, 2002, to Dobrin, et al.

As shown in FIG. 10, the deformation pattern can also be in the form of rib-like elements 84 that together define an array of spaced, circularly-shaped second regions 74. Each such circular element can be defined by appropriately spaced, varying-length rib-like elements 84 and intervening valleys 86. Between respective circularly-shaped elements 108 are unformed intervening first regions 72. As will be apparent to those skilled in the art, other deformation patterns can also be employed, if desired, such as those illustrated and described in U.S. Pat. No. 5,518,801.

Figure 11:
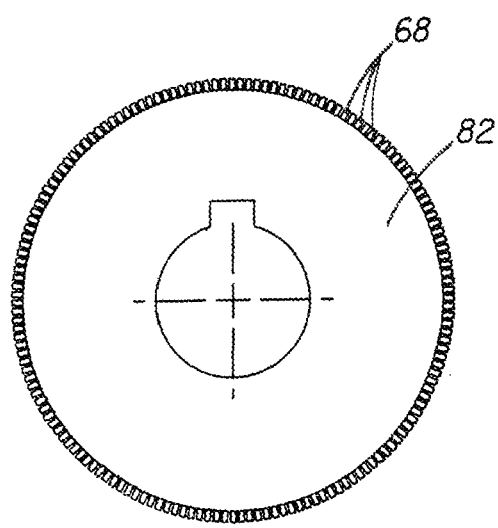
FIG. 11 is a side view of a roll for use in a micro-SELF process.

The third means for deforming a web of the present invention is a process that can best be described as "micro-SELF". Micro-SELF is a process that is similar in apparatus and method to that of the SELF process described with reference to FIGS. 6 and 7. The main difference between SELF and micro-SELF is the size and dimensions of the teeth 68 on the toothed roll, i.e., the micro-SELF roll 82 in FIG. 11, which corresponds to roll 62 of FIG. 6. Referring to FIG. 11 there is shown a schematic side view representation of a micro-SELF roll 82 that can be one of the rolls forming a nip roll arrangement in a preferred configuration having one patterned roll, e.g., micro-SELF roll 82, and one non-patterned grooved roll (not shown) similar to that shown as roll 64 in FIG. 6. However, in certain embodiments it may be preferable to use two micro-SELF roll 82 having either the same or differing patterns, in the same or different corresponding regions of the respective rolls. Such an apparatus can produce webs with deformations that, in nonwoven webs, can be described as tufts or loops protruding from one or both sides of the processed web. The tufts can be closely spaced, but at least at their base can be spaced apart sufficiently to define void region between tufts that permits fluid flow between adjacent tufts. The existing between tufts can define a continuous network of channels. In the micro-SELF roll of FIG. 11, individual teeth 68 can have a tooth length TL of about 0.051 inch (about 1.27 mm) with a distance between teeth TD of about 0.062 inch (about 1.57 mm) and a pitch of about 0.060 inch (about 1.52 mm). In one embodiment the circumference of roll 82 can be such that there are 158 teeth 68 separated by 159 cuts between teeth 68.

Figure 9:
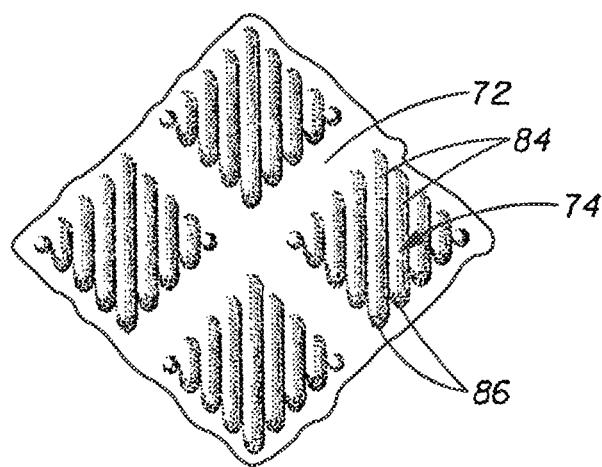
FIG. 9 is a pattern that can be produced in an absorbent material by passing the material between a pair of inter-meshing SELF rolls.
Figure 12:
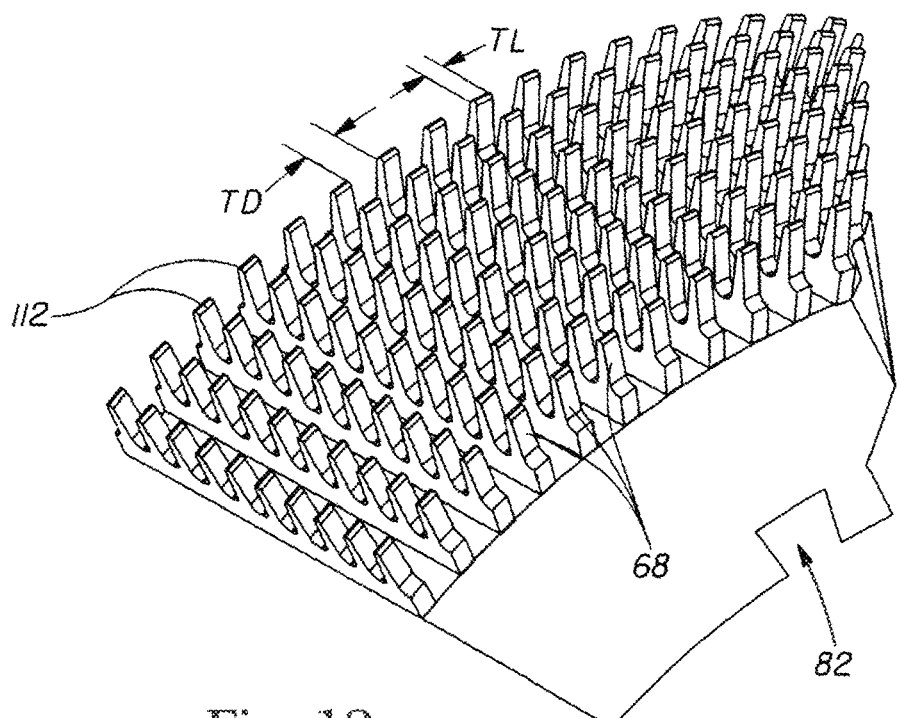
FIG. 12 is a perspective representation of roll for use in a micro-SELF apparatus.
Figure 13:
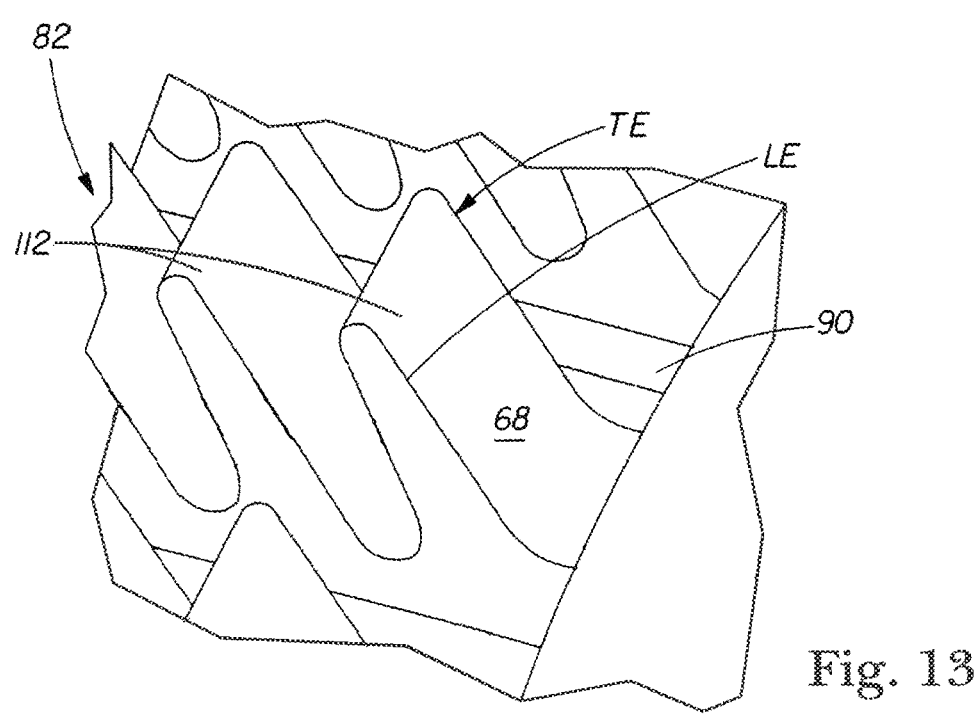
FIG. 13 is an enlarged perspective representation of the teeth on a micro-SELF roll.

As shown in the partial perspective view of FIG. 12 and the enlarged partial perspective view of FIG. 13, the teeth 68 of a micro-SELF roll 82 have a specific geometry associated with the leading and trailing edges of teeth 68 that permit the teeth to essentially "punch" through the nonwoven web 34 as opposed to, in essence, deforming the web into bumps or ridges as shown in FIGS. 8-10. In some embodiments of a nonwoven web 34 suitable for use in an absorbent core, the teeth 68 urge fibers out-of-plane and to form what can be described as "tufts" or loops of fibers. In one embodiment, the web is punctured, so to speak, by the teeth 68 pushing the fibers through to form tufts or loops. Therefore, unlike the "tent-like" rib-like elements of SELF webs which each have continuous side walls associated therewith, i.e., a continuous "transition zone," the tufts or loops forced out-of-plane in a micro-SELF process can have a discontinuous structure associated with the side wall portions of the Z-direction deformations. Additionally, when utilized for relatively high basis weight absorbent core materials, the "tufting" can be somewhat invisible as fibers are urged out of the plane in a Z-direction with respect to one of the web surfaces, the Z-direction deformation may be muted or non-existent in the other web surface. Further, when a laminate material is involved, the Z-direction deformations of one web material may be pushed into and "hidden" by the second material of the laminate, such that the "tufting" is essentially invisible to the naked eye.

Figure 14:
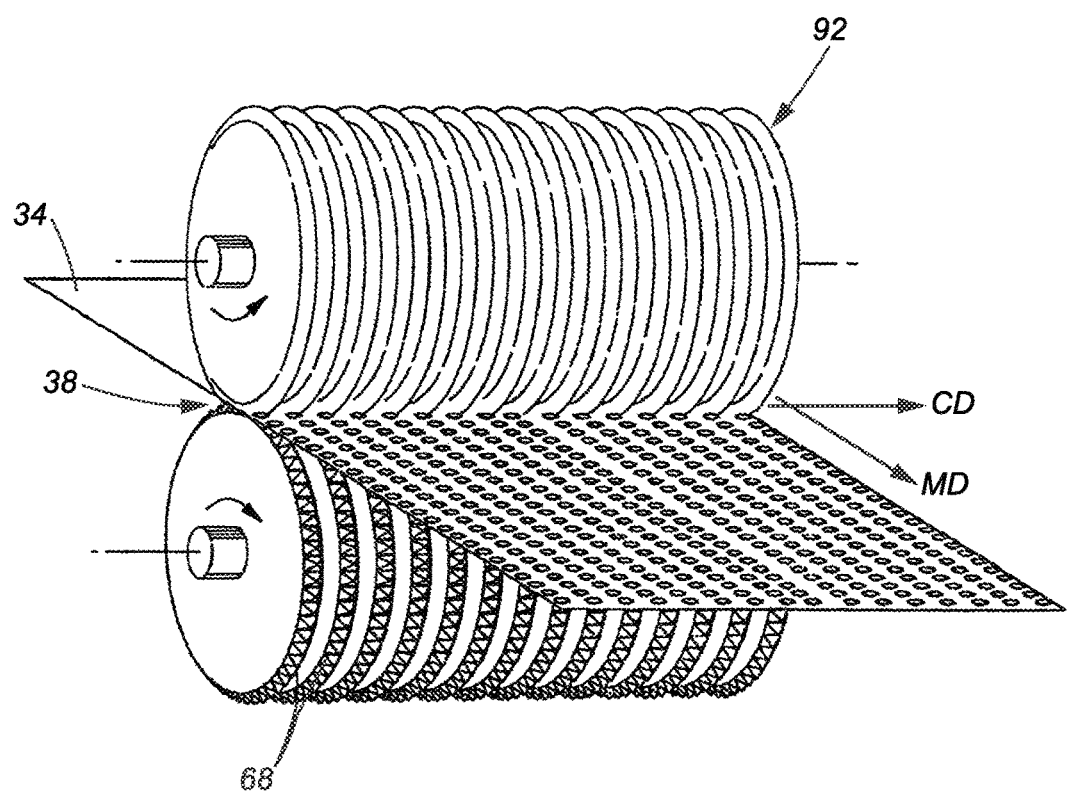
FIG. 14 is a schematic representation of a rotary knife apparatus (RKA) and process.

As shown in FIGS. 12 and 13, each tooth 68 has a tooth tip 112, a leading edge LE and a trailing edge TE. The tooth tip 112 is elongated and has a generally longitudinal orientation. It is believed that to get tufted, looped tufts in the processed web, the LE and TE should be very nearly orthogonal to the local peripheral surface 90 of roll 80. As well, the transition from the tip 112 and LE or TE should be a sharp angle, such as a right angle, having a sufficiently small radius of curvature such that teeth 68 push through web 34 (as shown in FIG. 14) at the LE and TE. Without being bound by theory, it is believed that having relatively sharply angled tip transitions between the tip 112 of tooth 68 and the LE and TE permits the teeth 68 to punch through nonwoven webs "cleanly", that is, locally and distinctly, so that one side of the resulting web can be described as "tufted" or otherwise "deformed."

The teeth 68 of a micro-SELF roll 82 can have a uniform circumferential length dimension TL measured generally from the leading edge LE to the trailing edge TE at the tooth tip 112 of about 1.25 mm and are uniformly spaced from one another circumferentially by a distance TD of about 1.5 mm. For processing a web having a total basis weight in the range of about 30 to about 500 gsm, teeth 110 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 6.4 mm (0.250 inches). Depth of engagement E can be from about 0.5 mm to about 5 mm (up to a maximum equal to tooth height TH). Of course, E, P, TH, TD and TL can be varied independently of each other to achieve a desired size, spacing, and area density of web deformations.

The fourth means for deforming a web suitable for use as an absorbent material is a process that can best be described as "rotary knife aperturing" (RKA). In RKA, a process and apparatus using counter-rotating meshing nip rolls 92 similar to that described above with respect to SELF or micro-SELF rolls is utilized, as shown in FIG. 14. As shown, the RKA process differs from SELF or micro-SELF in that the relatively flat, elongated teeth of a SELF or micro-SELF roll have been modified to be generally pointed at the distal end. Teeth 68 can be sharpened to cut through as well as deform nonwoven web 34 to produce a three-dimensionally apertured web 94 as shown in FIG. 14. In other respects such as tooth height, tooth spacing, pitch, depth of engagement, and other processing parameters, RKA and the RKA apparatus can be the same as described above with respect to SELF or micro-SELF.

Figure 15:
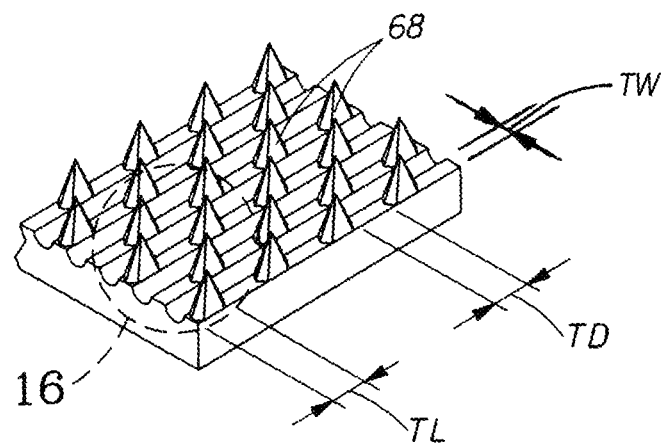
FIG. 15 is a portion of one embodiment of a roller of a rotary knife apparatus, the roller having a plurality of teeth useful for making an apertured web.
Figure 16:
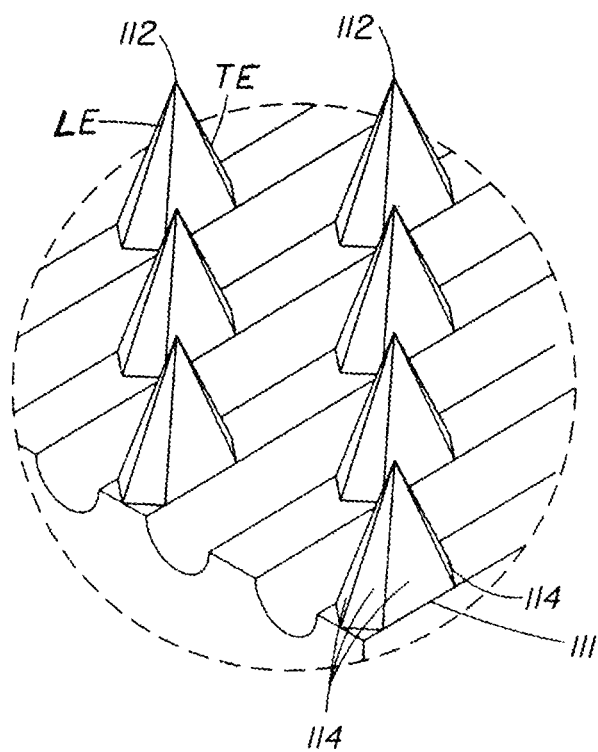
FIG. 16 is an enlarged perspective representation of one embodiment of teeth on the toothed roll of a rotary knife apparatus.
Figure 17:
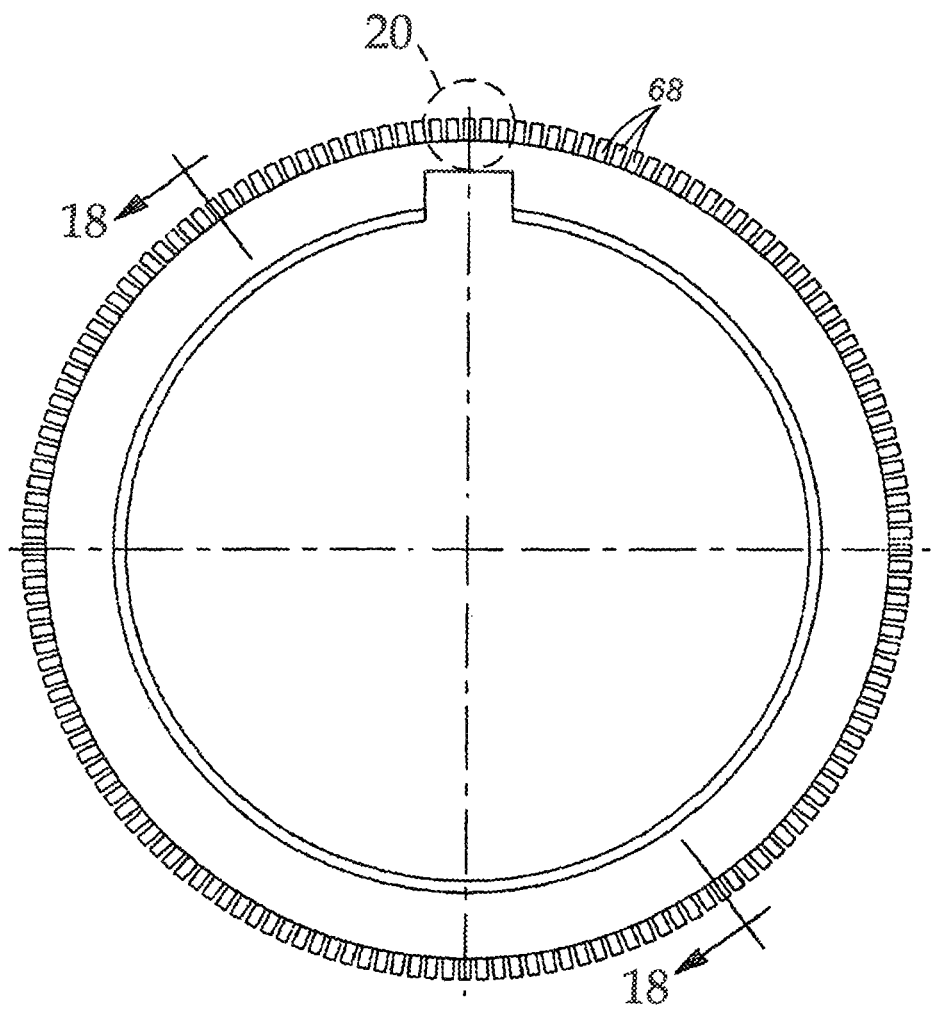
FIG. 17 is a side view of a SELF roll showing typical dimensions useful in some embodiments of the present invention.
Figure 18:
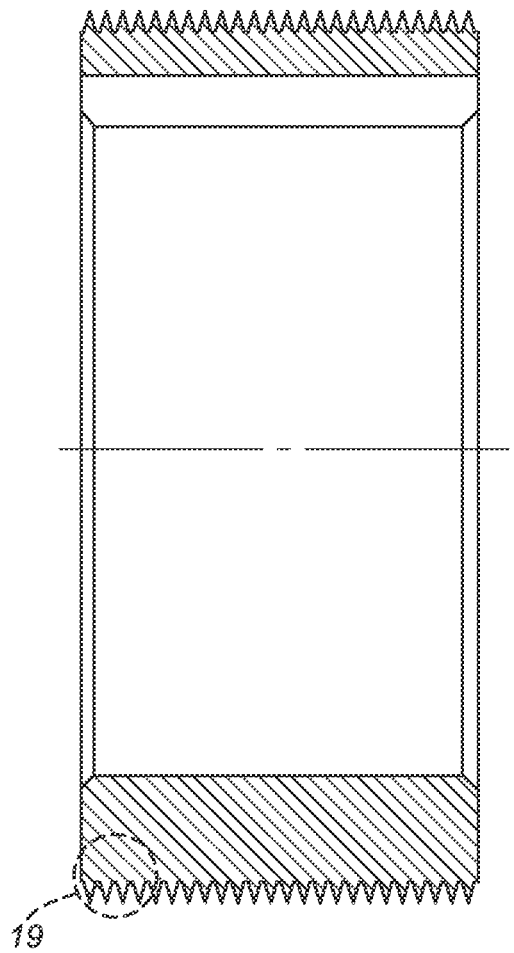
FIG. 18 is a cross-sectional view of the roll shown in FIG. 17, taken along line 18-18, showing typical dimensions useful in some embodiments of the present invention.

FIG. 15 shows a portion of one embodiment of an RKA toothed roller having a plurality of teeth 68 useful for making an apertured web 94. An enlarged view of the teeth 68 is shown in FIG. 16. As shown in FIGS. 15 and 16, each tooth 68 has a base 111, a tooth tip 112, a leading edge LE and a trailing edge TE. The tooth tip 112 can be generally pointed, blunt pointed, or otherwise shaped so as to stretch and/or puncture the precursor web 34. Teeth 68 can have generally flattened, blade-like shape. Teeth 68 can have generally flattened distinct sides 114. That is, as opposed to round, pin-like shapes that are generally round in cross section, teeth 68 can be elongated in one dimension, having generally non-round, elongated cross-sectional configurations. For example, at their base, teeth 110 can have a tooth length TL and a tooth width TW exhibiting a tooth aspect ratio AR of TL/TW of at least 2, or at least about 3, or at least about 5, or at least about 7, or at least about 10 or greater. In one embodiment, the aspect ratio AR of cross-sectional dimensions remains substantially constant with tooth height.

In one embodiment of an RKA toothed roll, teeth 68 can have a uniform circumferential length dimension TL of about 1.25 mm measured generally from the leading edge LE to the trailing edge TE at the base 111 of the tooth 110, and a tooth width TW of about 0.3 mm which is the longest dimension measured generally perpendicularly to the circumferential length dimension at the base. Teeth can be uniformly spaced from one another circumferentially by a distance TD of about 1.5 mm. For making a soft, fibrous three-dimensional apertured web from a precursor web 20 having a basis weight in the range of from about 5 gsm to about 500 gsm, teeth 68 can have a length TL ranging from about 0.5 mm to about 3 mm, a tooth width TW of from about 0.3 mm to about 1 mm, and a spacing TD from about 0.5 mm to about 3 mm, a tooth height TH ranging from about 0.5 mm to about 10 mm, and a pitch P between about 1 mm (0.040 inches) and 2.54 mm (0.100 inches). Depth of engagement E can be from about 0.5 mm to about 5 mm (up to a maximum approaching the tooth height TH).

Of course, DOE, P, TH, TD and TL can each be varied independently of each other to achieve a desired size, spacing, and area density of apertures (number of apertures per unit area of apertured three-dimensionally apertured). For example, to make apertured films and nonwovens suitable for use in sanitary napkins and other absorbent articles, tooth length TL at the base can range between about 2.032 mm to about 3.81 mm; tooth width TW can range from about 0.508 mm to about 1.27 mm; tooth spacing TD can range from about 1.0 mm to about 1.94 mm; pitch P can range from about 1.106 mm to about 2.54 mm; and tooth height TH can be from about 2.032 mm to about 6.858 mm Depth of engagement DOE can be from about 0.5 mm to about 5 mm. The radius of curvature R of the tooth tip 112 can be from 0.001 mm to about 0.009 mm Without being bound by theory, it is believed that tooth length TL at the base can range between about 0.254 mm to about 12.7 mm; tooth width TW can range from about 0.254 mm to about 5.08 mm; tooth spacing TD can range from about 0.0 mm to about 25.4 mm (or more); pitch P can range from about 1.106 mm to about 7.62 mm; tooth height TH can range from 0.254 mm to about 18 mm; and depth of engagement E can range from 0.254 mm to about 6.35 mm. For each of the ranges disclosed, it is disclosed herein that the dimensions can vary within the range in increments of 0.001 mm from the minimum dimension to the maximum dimension, such that the present disclosure is teaching the range limits and every dimension in between in 0.001 mm increments (except for radius of curvature R, in which increments are disclosed as varying in 0.0001 mm increments).

RKA teeth can have other shapes and profiles and the RKA process can be used to aperture fibrous webs, as disclosed in co-pending, commonly owned patent applications US 2005/0064136A1, filed Aug. 6, 2004, US 2006/0087053A1, filed Oct. 13, 2005, and US 2005/021753 filed Jun. 21, 2005.

Each of the web deforming processes described above is known in the art for processing various webs of an absorbent article. For example, ring rolling is known to be used in combination with a thermal melt weakening step to produce apertures, as disclosed in U.S. Pat. Nos. 5,628,097 and 5,916,661, and US 2003/0028165A1. As well, the SELF process is well known for making stretch portions of a topsheet as disclosed in US 2004/0127875A1, filed Dec. 18, 2002. Micro-SELF rolls are known to produce beneficially-modified topsheets as disclosed in US 2004/0131820A1, WO 2004/059061A1 and WO 2004/058118A1. And RKA is known to produce apertured formed films, nonwoven webs, and laminates, as disclosed in US 2005/021753. Absorbent cores have also been modified by micro-SELF rolls as disclosed in WO 2004/058497A1 in which a laminate of two webs is made by processing two webs together to form a fiber-integrated composite absorbent core.

In each of the processes described above heat can be utilized, either by heating the web before the nip of the rollers or by way of heated rollers, or heating the web after leaving the nip rollers. If any of the rollers of the apparatuses as described above are to be heated, care must be taken to account for thermal expansion. In one embodiment, the dimensions of ridges, grooves, and/or teeth are machined to account for thermal expansion, such that the dimensions described herein can be dimensions at operating temperature.

In one embodiment, processing of an absorbent core material can be achieved by the method disclosed in commonly-owned, co-pending US Application No. 2006/0286343A1 entitled Tufted Fibrous Web. This method can include a heating means in which the tips, or distal ends, of web features such as ribs or tufts can be heated and/or bonded. Such heating and/or bonding can increase the crush-resistance of an absorbent core, and can improve its resiliency, which is important for maintaining permeability under pressure. Resiliency can be improved by incorporating thermoplastic bonding powders, such as polyethylene powder into the fibrous web, and then heating in regions where bonding is desired. Resiliency can also be improved by application of coatings, such as latex coatings, that can tend to stiffen fibers, for example.

In one embodiment, multiple absorbent core layers can be integrated by inter-entangling fibers from adjacent webs. Fiber entanglement of adjacent layers can be achieved by the processes described herein, and also by known means such as needle-punching, hydroentangling, and thermal point bonding. By the same processes and means, it may be desirable to integrate the topsheet of an absorbent article with an underlying layer, such as a secondary topsheet modified by the processes disclosed herein.

While the various web deforming processes described above are known for topsheets, backsheets, and composite absorbent cores, the novel feature of the present invention is the application of these processes to achieve unexpected fluid handling property results in absorbent homogeneous webs processed individually to be heterogeneous, and then combined in a layered relationship with other webs that can also have been processed by a web deforming process to be heterogeneous. Combined webs need not be affixed in a joined relationship, but can be joined if desired by means known in the art, such as by adhesive bonding, thermal bonding, fiber entangling, latex bonding, and combinations thereof. The invention is believed to be applicable to a wide variety of fibers, including bicomponent fibers, nano-fibers, shaped fibers, and combinations thereof, as well as a wide variety of webs by various forming processes, including meltblown, spunbond, and carded webs, wet-laid webs including tissue paper, or combinations of these processes. The invention is described below in a specific embodiment of airlaid absorbent fibrous webs, i.e., core materials made by air laying processes.

Air laying is a process for making nonwoven webs in which cut staple fibers are introduced into an air stream which forces the fibers onto a laydown belt in a controlled manner. The fibers may be natural or synthetic, and may be bonded by thermal, chemical, or mechanical means into a consolidated nonwoven web. When fibers are supplied as cut, stable fibers in compacted form, the airlaid process begins with a defibration system to open and feed the staple fibers into an air stream. Other functions can also be carried out, such at the dosage and introduction of super absorbents or other powders. The fibrous and/or other materials are suspended in air within a forming system and subsequently deposited onto a moving forming screen or rotating perforated cylinder to form a randomly oriented air formed batt. The air formed batt can be bonded by applying latex binder and drying, thermally bonding thermoplastic staple fibers in the web, hydrogen or embossed bonding or a combination of these consolidation techniques. Airlaid web formation is taught in U.S. Pat. No. 4,640,810, to Laursen et al. Airlaid webs can be made by air laying a blend of fibrous materials, or by air laying discrete layers, each layer having a different type or blend of fibers.

In general, known methods of making airlaid materials produce homogeneous webs of airlaid material. As used herein, "homogeneous" refers to the uniformity of the web in the MD-CD plane, as indicated in FIG. 14, for example. As shown in FIG. 14, prior to formation through nip 38, web 34 can be formed by a typical airlaid process so that in the MD-CD plane the web is substantially uniform in bulk properties such as density and basis weight. Virtually any discrete region chosen in the MD-CD plane of a homogeneous web would have the same material handling properties as an immediately adjacent region. Note that homogeneous does not refer to the nature of the web in the "Z-direction," i.e., in a direction perpendicular to the MD-CD plane, which can be considered as being the thickness of the web. Web properties can vary in the Z-direction by layering fibers in a non-uniform manner through the thickness of the web.

As used herein, "heterogeneous" refers to the non-uniformity of the web in the MD-CD plane, as indicated in FIG. 14, for example. As shown in FIG. 14, after formation through nip 38, web 34 has been rendered heterogeneous such that in the MD-CD plane the web is substantially non-uniform in bulk properties such as density and basis weight. Discrete regions of the web have been mechanically deformed into tufts, apertures, or other three-dimensionally formed structures, such that discrete portions of the web in the MD-CD plane would have the very different material handling properties compared to immediately adjacent regions.

The size of the discrete portions under consideration can vary depending on the size of the web and the purpose of the heterogeneous web. In general, however, it is desirable to have closely spaced discrete portions on the order of from about 1 to about 30 per square centimeter, including every whole number in between, including from about 5 to about 10 per square centimeter. By having relatively closely spaced (in the MD-CD plane) discrete portions in the form of ribs, tufts, or apertures, for example, fluid handling is improved by increasing the probability that a given drop of fluid on the web can experience both high permeability and high capillarity options upon contact with the web.

To illustrate the present invention, generally homogeneous absorbent airlaid fibrous web materials were modified by one or more of the four processes described above to achieve a heterogeneous absorbent core material having the ability to advantageously move fluid rapidly into secure storage in the absorbent core when used in a sanitary napkin. In one aspect, the heterogeneity of the absorbent core permits the core to exhibit fluid moving properties generally laterally, that is, in the plane of the web material. That is, rather than exhibit heterogeneity in the Z-direction, i.e., in a direction through the thickness of the web, the web of the present invention can exhibit heterogeneity in the "X-Y" plane, i.e., in a plane parallel with the plane of the web in generally flattened condition, referred to herein as lateral fluid movement.

Tables 1 and 2 below illustrate the benefits of processing an airlaid fibrous absorbent material by one or more of the four formation means described above. For all dimensions 1 inch equals 25.4 mm.

Table 1 shows variations in fluid handling properties for a web referred to herein as Absorbent Core I, made from an unmodified precursor web described in Table 1 as Control Absorbent I. The Control Absorbent I web is an airlaid absorbent core material having a basis weight of about 180 grams per square meter (gsm) and comprising cellulosic fibers and bicomponent fibers blended in an air laying process together with 30 gsm of absorbent gelling material (AGM). The cellulosic fibers are Weyco NB416 obtained from Weyerhaeuser Co. The bicomponent fibers are Invista #35160A (PE/PET, 2.0 denier and 4 mm length) obtained from Invista and the proportion of cellulosic fibers to bicomponent fibers is 5 gram to 1 gram. The AGM is Degussa 23070G obtained from Degussa, and is dispersed substantially uniformly throughout the web. About 5 wt % latex AF 192 obtained from Air Products is sprayed on the surface of both sides and allowed to cure.

Table 2 shows variations in fluid handling properties for a web referred to herein as Absorbent Core II, made from an unmodified precursor web described in Table 1 as Control Absorbent II. The Control Absorbent II is an airlaid absorbent material suitable for use as a secondary topsheet and is a laminate having a basis weight of about 82 grams per square meter (gsm). One layer of the laminate of Control Absorbent II is a spunbond polypropylene (PP) hydrophilic nonwoven having a basis weight of about 22 gsm. The spunbond web layer can be obtained as P9 from Fiberweb. The spunbond polypropylene web is laminated to a web produced in an air laying process, the air laid web being a 60 gsm web of cellulosic fibers and polyethylene powder binder blended in the air laying process. About 5 wt % latex AF 192 obtained from Air Product was sprayed on the surfaces of the air laid web prior to lamination to the spunbond material. The cellulosic fibers are Weyco NB416 obtained from Weyerhaeuser Co. The polyethylene powder binder is Dow Low Density polyethylene 959s obtained from Dow, and the proportion of cellulosic fibers to polyethylene powder binder is 3 g to 1 g. After air laying, the laminate web is processed through a heating step to effect the binding properties of the polyethylene binder powder.

As shown in Table 1, the absorption capillary pressure and desorption capillary pressure, the grams per gram capacity, the permeability, and the flow rate can each be changed in a beneficially positive manner by formation by the denoted processes. Each of the parameters were determined by the tests shown in the Test Methods section below.

TABLE 1

Fluid Handling Properties of Modified Airlaid Fibrous Absorbent Core I

| Sample No. | Formation Process Type | Absorption Capillary Potential (mJ/m$^2$) | Desorption Capillary Potential (mJ/m$^2$) | Capacity (g/g) | Permeability (Darcy's) | Flow Rate (g/sec) |
|---|---|---|---|---|---|---|
| 1 | Control Absorbent I | 636 | 1111 | 4.14 | 171 | 5.65 |
| 2 | SELF | 707 | 1297 | 6.76 | 360 | 8.8 |
| 3 | SELF | 632 | 1257 | 6.04 | 271 | 7.66 |
| 4 | RKA | 677 | 1167 | 5.03 | 240 | 6.96 |
| 5 | SELF | 732 | 1260 | 6.01 | 348 | 9.12 |
| 6 | SELF | 614 | 1172 | 6.15 | 399 | 11 |

Figure 19:
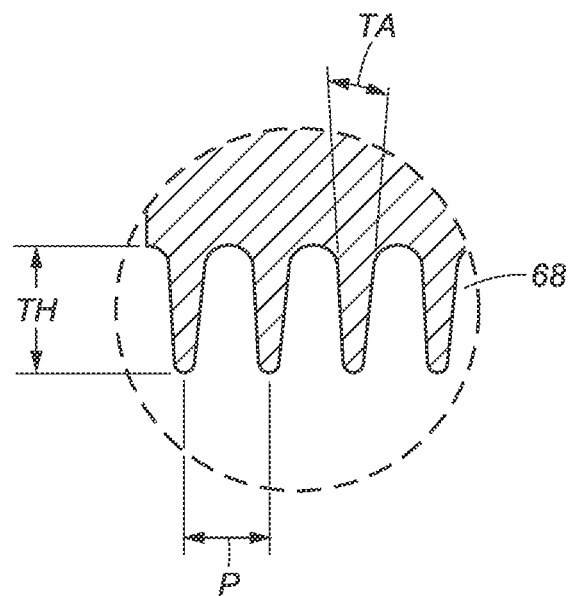
FIG. 19 is a cross-sectional view of the teeth of a SELF roll showing typical dimensions useful in some embodiments of the present invention.
Figure 20:
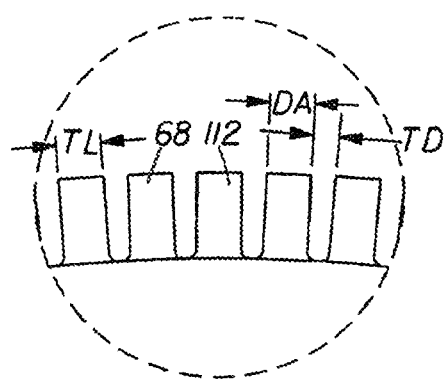
FIG. 20 is an enlarged side view of the teeth of the roll shown in FIG. 17, showing typical dimensions useful in some embodiments of the present invention.

Sample No. 2 was made by processing Control Absorbent I through a SELF'ing process in which the toothed roll had the dimensions shown in FIGS. 17-20. As shown in FIG. 19, the teeth had a pitch P of 0.100 inches, a tooth height TH of about 6.86 mm (about 0.270 inches), and a tooth angle TA between teeth of about 9.478 degrees. As shown in FIG. 20, each tooth had a tooth length TL of about 5.33 mm (about 0.2101 inches), a tooth spacing TD of about 1.98 mm (about 0.0781 inches), and a diverging tooth angle DA of about 2.903 degrees. The mating roll was an un-toothed roll, that is, a roll having circumferentially extending ridges and grooves, similar to that shown in FIG. 6 above, and engaged at a DOE of about 1.78 mm (about 0.070 inch). The SELF'ing process was carried out at room temperature at a rate of about 1-5 m/min.

Figure 21:
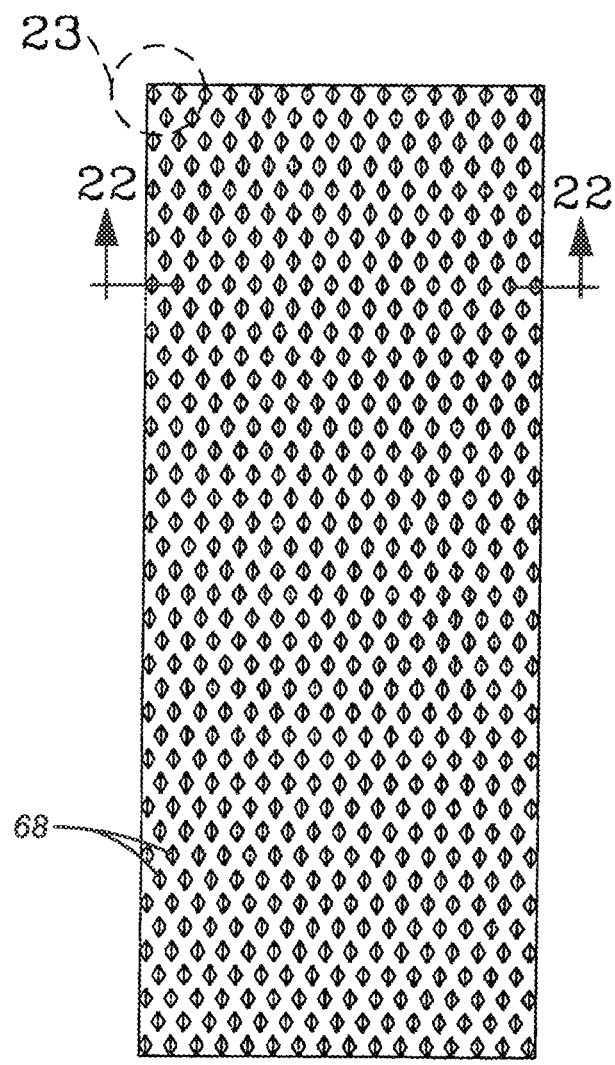
FIG. 21 is a flat layout view of an SELF roll having a staggered tooth pattern and showing typical dimensions useful in some embodiments of the present invention.
Figure 22:
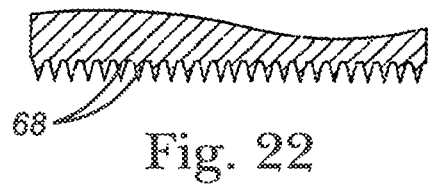
FIG. 22 is a cross-sectional view of a portion of the SELF roll shown in FIG. 20, taken along line 22-22.
Figure 23:
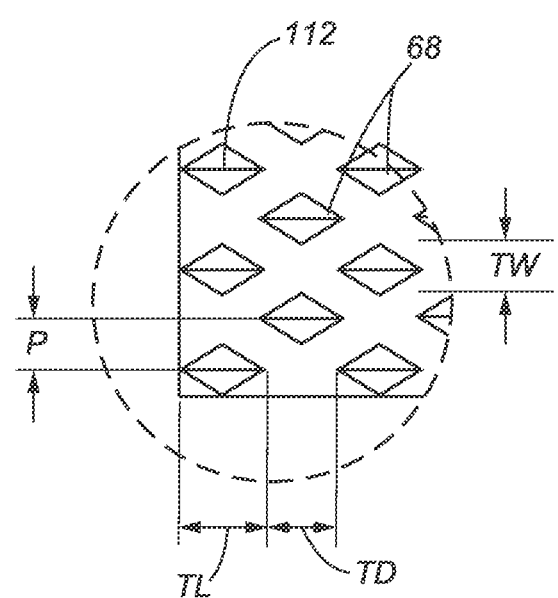
FIG. 23 is an enlarged plan view of some of the teeth of the SELF roll shown in FIG. 20 showing typical dimensions useful in some embodiments of the present invention.
Figure 24:
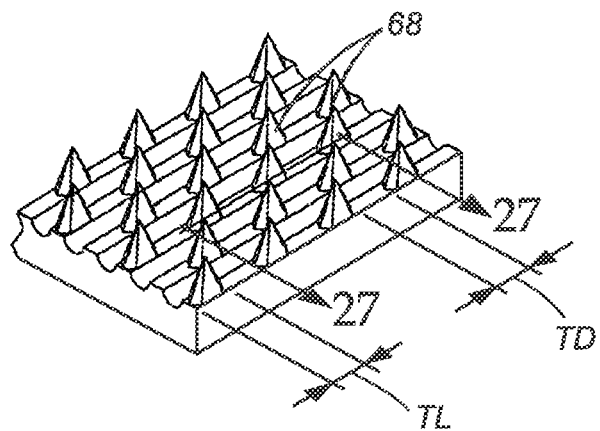
FIG. 24 is a partial perspective view showing one embodiment of teeth on an RKA roll, and showing typical dimensions useful in some embodiments of the present invention (in mm).
Figure 25:
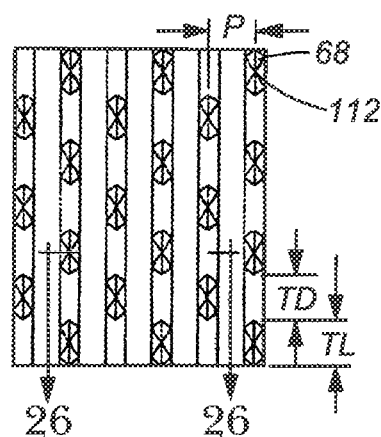
FIG. 25 is a plan view of the teeth of an RKA roll as shown in FIG. 24, and showing typical dimensions useful in some embodiments of the present invention (in mm).

Sample No. 3 was made by processing Control Absorbent I through a SELF'ing process in which the toothed roll had dimensions as shown in FIGS. 21-23. FIG. 21 is a flat-out view of the circumference of a toothed roll. One difference from the tooth configuration of the rolls shown in FIGS. 21-23 and those used to make Sample 2 is that the teeth, rather than having a generally rectangular shape when viewed from the top (i.e., in plan view, looking down on the surface of the roll), each tooth has a generally diamond shape as shown in FIG. 23. Also, the pitch P from tooth to tooth in a row is 0.200 inch, which results in a 0.100 pitch P from tooth to tooth in a stagger pattern. Teeth 68 have a tooth length TL of about 5 mm, and a tooth distance TD of about 4 mm. The mating roll was an un-toothed roll, that is, a roll having circumferentially extending ridges and grooves, similar to that shown in FIG. 6 above, wherein the two mating rolls meshed at a DOE of about 1.78 mm (about 0.070 inch). The SELF'ing process was carried out at room temperature at a rate of about 1-5 m/min.

Figure 26:
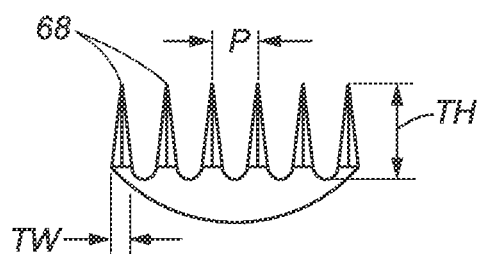
FIG. 26 is a cross-sectional view of teeth on an RKA roll of FIG. 24 taken along line 26-26 of FIG. 25, and showing typical dimensions useful in some embodiments of the present invention (in mm).
Figure 27:
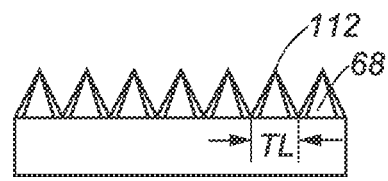
FIG. 27 is a cross-sectional view of teeth on an RKA roll of FIG. 24 taken along line 27-27 of FIG. 24, and showing typical dimensions useful in some embodiments of the present invention (in mm).

Sample No. 4 was made by processing Control Absorbent I through a RKA process in which the toothed roll had teeth having the dimensions shown in FIGS. 24-27. As shown in FIGS. 24-27, the teeth of the toothed RKA roll were configured in a staggered pattern having a row to row pitch P of about 2.54 mm (about 0.100 inch). The teeth 68 have a tooth length (measured at the base) TL of about 3.81 mm (about 0.150 inch) and a tooth distance TD of about 1.94 mm (about 0.076 inch). As shown in FIG. 26, teeth 68 have a tooth width at the base of about 1.27 mm and a tooth height TH of about 6.858 mm (about 0.270 inch). The mating roll was an un-toothed roll, that is, a roll having circumferentially extending ridges and grooves, similar to that shown in FIG. 6 above, and engaged at a DOE of about 6.35 mm (about 0.250 inch). The RKA process was carried out at room temperature at a rate of about 1-5 m/min.

Figure 28:
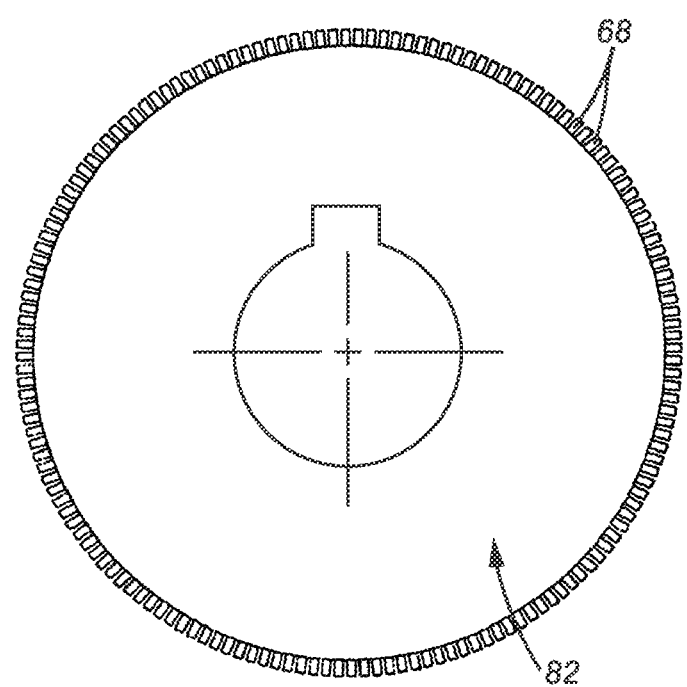
FIG. 28 is a side view of a SELF roll suitable for the present invention.
Figure 29:
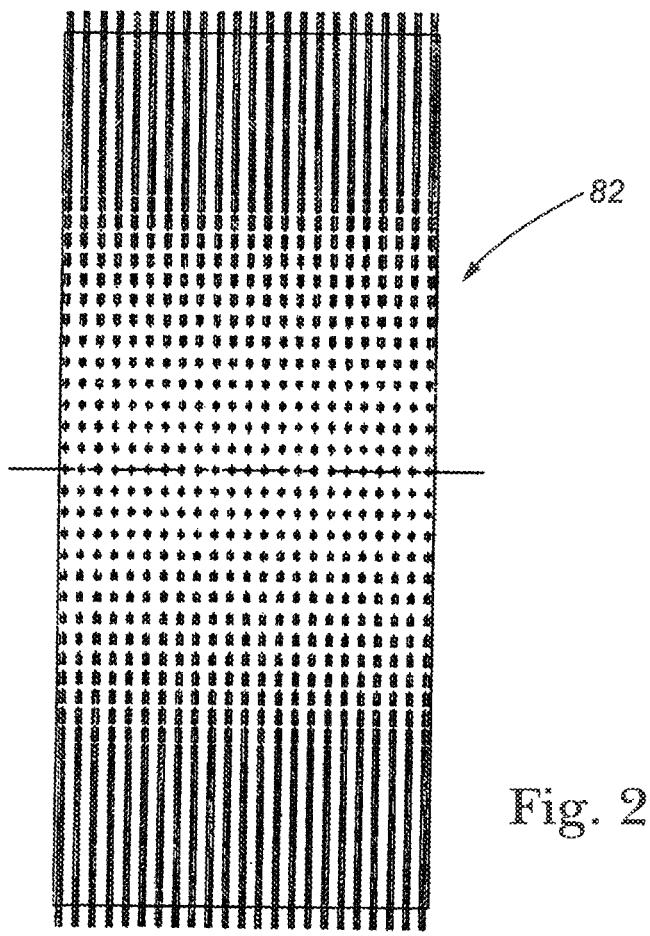
FIG. 29 is a view of the outer surface of the SELF roll shown in FIG. 28.
Figure 30:
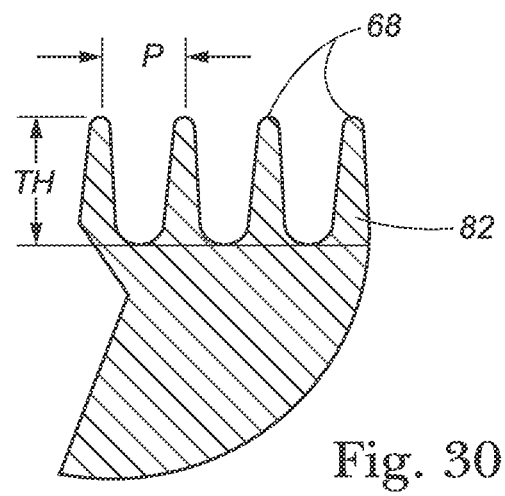
FIG. 30 is a schematic detail of the teeth of the roll shown in FIGS. 28 and 29, and showing typical dimensions (in inches).
Figure 31:
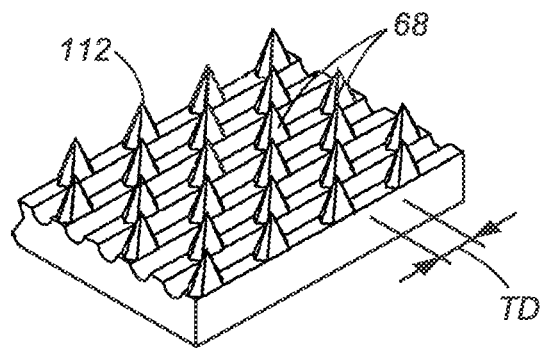
FIG. 31 is a partial perspective view showing one embodiment of teeth on an RKA roll, and showing typical dimensions useful in some embodiments of the present invention (in mm).
Figure 32:
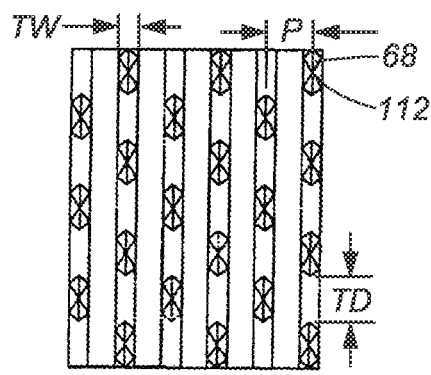
FIG. 32 is a plan view of a portion of the RKA roll shown in FIG. 31, and showing typical dimensions useful in some embodiments of the present invention (in mm).
Figure 33:
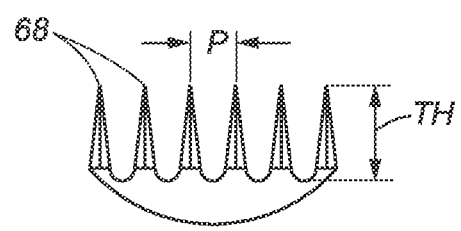
FIG. 33 is a partial cross-sectional view of 33-33 in FIG. 32 showing one embodiment of teeth on an RKA roll, and showing typical dimensions useful in some embodiments of the present invention (in mm).
Figure 34:
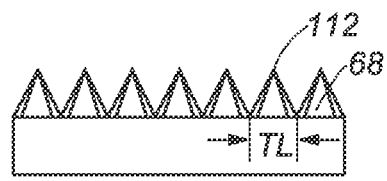
FIG. 34 is a side view showing the teeth in FIG. 31, and showing typical dimensions useful in some embodiments of the present invention (in mm).
Figure 35:
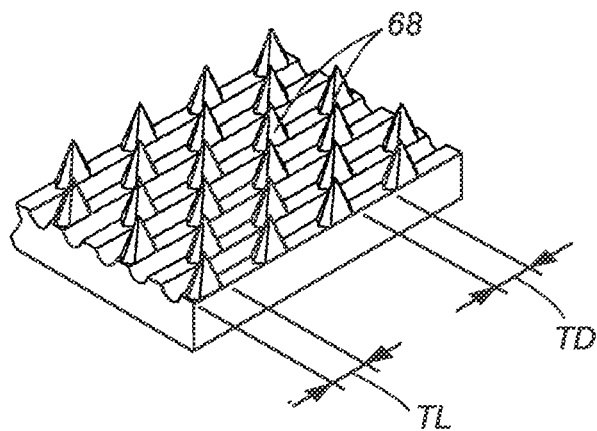
FIG. 35 is a partial perspective view showing one embodiment of teeth on an RKA roll, and showing typical dimensions useful in some embodiments of the present invention (in mm).
Figure 36:
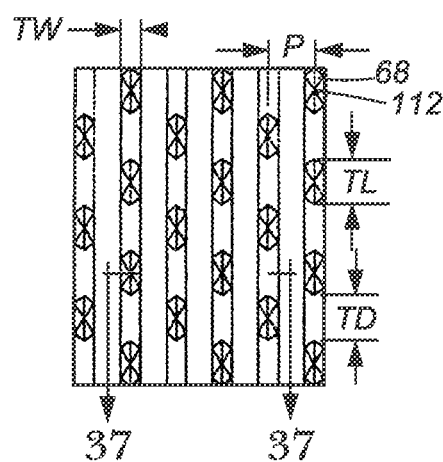
FIG. 36 is a plan view of a portion of the RKA roll shown in FIG. 35, and showing typical dimensions useful in some embodiments of the present invention (in mm).
Figure 37:
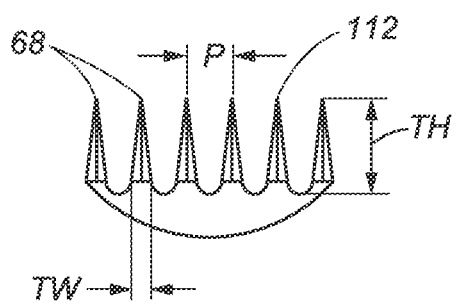
FIG. 37 is a partial cross-sectional view of 37-37 in FIG. 36 showing one embodiment of teeth on an RKA roll, and showing typical dimensions useful in some embodiments of the present invention (in mm).
Figure 38:
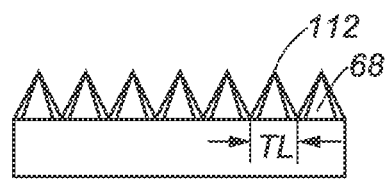
FIG. 38 is a side view showing the teeth in FIG. 35, and showing typical dimensions useful in some embodiments of the present invention (in mm).

Sample 5 was made by processing Control Absorbent I through a SELF'ing process in which the toothed roll had a configuration shown in FIGS. 28-30. The teeth 68, rather than being in straight rows across the width of the roll, are placed in staggered groups of three teeth that make a generally circular shape to form a pattern on a processed web similar to that shown in FIG. 10. As shown in FIG. 30, teeth 68 have a tooth height TH of about 3.6 mm (0.145 inches) and a pitch P of about 1.524 mm (about 0.060 inch). The toothed roll was engaged with a mating ring roll having fully circumferential ridges and grooves similar to that shown in FIG. 6 above, engaged at a DOE of about 1.9 mm (about 0.075 inch). The SELF'ing process was carried out at room temperature at a rate of about 1-5 m/min.

Sample 6 was made by processing Control Absorbent I through a modified SELF'ing process in which an upper toothed roll had the configuration described for the toothed roll of Sample 5. However, the inter-meshing (inter-engaging) roll, rather than having fully circumferential ridges and grooves similar to that shown in FIG. 6 above, was another toothed micro-SELF'ing roll similar to that shown in FIGS. 11-13, with a pitch of about 1.52 mm (about 0.060 inch) to match the upper toothed roll. The rolls were operated at a DOE of about 1.65 mm (about 0.065 inch). The process was carried out at room temperature at a rate of about 1-5 m/min.

As can be seen in Table 1, in all cases the grams (of absorbed fluid) per gram (of absorbent material) capacity, the permeability and the flow rate, all increased significantly, as did the capillary pressure in most cases. All these improvements are a result of simply processing a web material through the nip of a pair of intermeshing (or inter-engaging) rollers as described above. Therefore, there is no new material content or new composition that would increase costs associated with the much better fluid acquisition properties.

TABLE 2

Fluid Handling Properties of Modified Airlaid Fibrous Absorbent Core II

| Sample No. | Formation Process Type | Absorption Capillary Potential (mJ/m$^2$) | Desorption Capillary Potential (mJ/m$^2$) | Capacity (g/g) | Permeability (Darcy's) | Flow Rate (g/sec) |
|---|---|---|---|---|---|---|
| 7 | Control Absorbent II | 301 | 596 | 3.75 | 106 | 15 |
| 8 | Ring roll | 321 | 683 | 5.39 | 201 | 22 |
| 9 | SELF | 323 | 738 | 10.43 | 327 | 13 |
| 10 | micro-SELF | 342 | 724 | 8.59 | 204 | 18 |
| 11 | micro-SELF | 324 | 696 | 6.07 | 185 | 18 |
| 12 | RKA | 323 | 496 | 6.71 | 204 | 24 |
| 13 | RKA | 343 | 649 | 6.39 | 174 | 19 |
| 14 | RKA | 316 | 644 | 6.8 | 175 | 20 |
| 15 | RKA | 321 | 651 | 5.39 | 121 | 16 |
| 16 | SELF | 322 | 657 | 8.24 | 165 | 15 |
| 17 | SELF | 309 | 670 | 8.54 | 246 | 21 |
| 18 | SELF | 295 | 672 | 7.39 | 186 | 17 |
| 19 | 1$^{st}$ pass: Ring roll 2$^{nd}$ pass: RKA | 361 | 641 | 7.68 | 208 | 23 |
| 20 | 1$^{st}$ pass: μ-SELF 2$^{nd}$ pass: RKA | 367 | 757 | 8.58 | 252 | 20 |
| 21 | 1$^{st}$ pass : μ-SELF 2$^{nd}$ pass: RKA | 340 | 742 | 8.16 | 254 | 20 |

Figure 3:
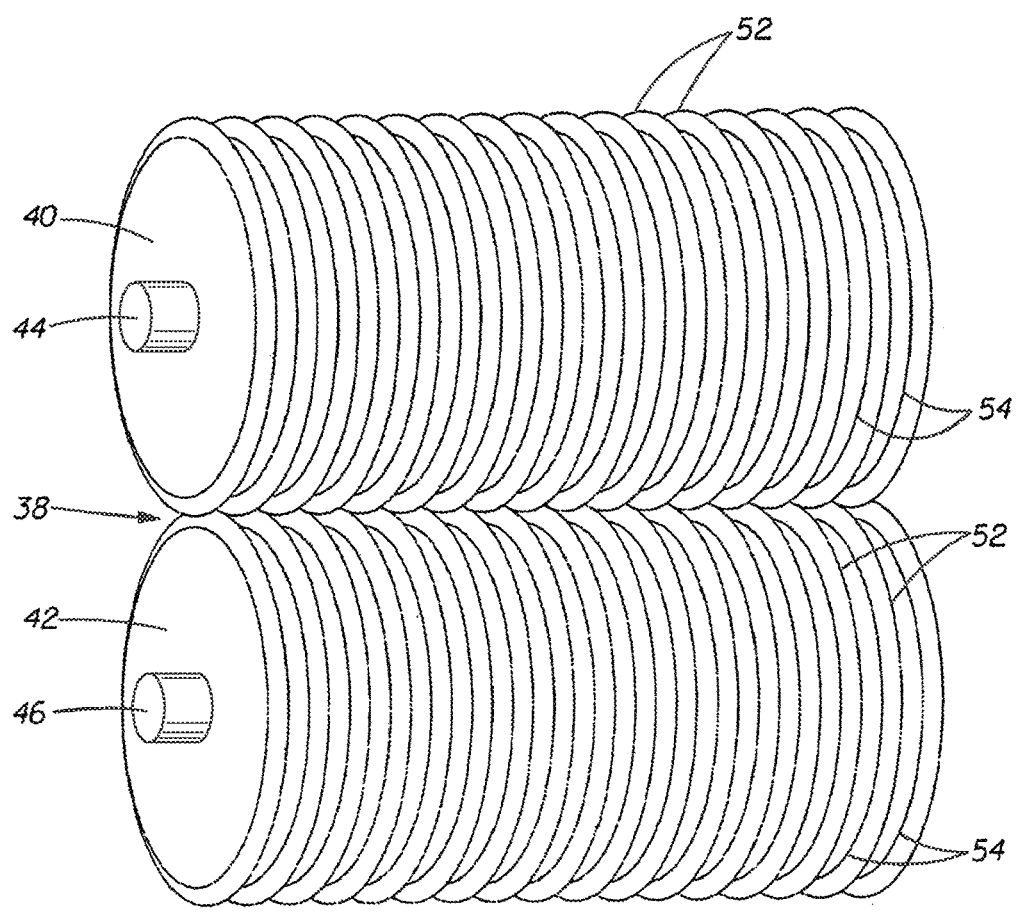
FIG. 3 is schematic representation of a pair of inter-meshing rolls of a process commonly referred to as ring-rolling.

Sample No. 8 was made by processing Control Absorbent II through a ring rolling apparatus as described with reference to FIGS. 2 and 3. The ring rolls had a pitch of about 1.016 mm (about 0.040 inch) and were meshed at a DOE of about 1.016 mm (about 0.040 inch). The process was carried out at room temperature.

Sample 9 was made by processing Control Absorbent II through intermeshing SELF rollers as described for Sample 2 above, with a DOE of about 2.45 mm (about 0.100 inch). The spunbond PP side of Control Absorbent II faced the non-toothed roll of the apparatus. The process was carried out at room temperature.

Sample 10 was made by processing Control Absorbent II through intermeshing micro-SELF rollers having a pitch P of about 1.52 mm (about 0.060 inch) as described with respect to FIG. 11, and with a DOE of about 1.9 mm (about 0.075 inch). The spunbond PP side of Control Absorbent II faced the non-toothed roll of the apparatus. The process was carried out at room temperature.

Sample 11 was made by processing Control Absorbent II through intermeshing micro-SELF rollers having a pitch of about 1.52 mm (about 0.060 inch) as described with respect to FIG. 11, and with a DOE of about 3.43 mm (about 0.135 inch). The spunbond PP side of Control Absorbent II faced the toothed micro-SELF roll of the apparatus. The process was carried out at a temperature of 300 degrees F.

Sample 12 was made by processing Control Absorbent II through an RKA process in which the toothed roll had teeth having the dimensions shown in FIGS. 31-34. The spunbond PP side of Control Absorbent II faced the RKA roll of the apparatus. As shown in FIGS. 31-34, the teeth of the toothed RKA roll were configured in a staggered pattern having a row to row pitch of about 1.016 mm (about 0.040 inch). Both the tooth height TH and tooth length TL were each about 2.032 mm (about 0.080 inch). Tooth distance TD was about 1.626 mm (about 0.64 inch) and the tooth width TW was about 0.510 mm (about 0.020 inch) Other dimensions were as shown. The mating roll was an un-toothed roll, that is, a roll having circumferentially extending ridges and grooves, similar to that shown in FIG. 6 above at a DOE of about 6.35 mm (about 0.250 inch). The RKA process was carried out at a temperature of 250 degrees F. at a rate of about 1-5 m/min.

Sample 13 was made by processing Control Absorbent II through an RKA process in which the toothed roll had teeth having the dimensions shown in FIGS. 35-38. The spunbond PP side of Control Absorbent II faced the RKA roll of the apparatus. As shown in FIGS. 35-38, the teeth 68 of the toothed RKA roll were configured in a staggered pattern having a row to row pitch P of about 1.524 mm (about 0.060 inch). The tooth height TH was about 3.683 mm (about 0.145 inch), the tooth distance TD was about 1 mm (about 0.039 inch), and the tooth length TL was about 2.032 mm (about 0.080 inch). Other dimensions were as shown. The mating roll was an un-toothed roll, that is, a roll having circumferentially extending ridges and grooves, similar to that shown in FIG. 6 above at a DOE of about 3.43 mm (about 0.135 inch). The RKA process was carried out at a temperature of 300 degrees F. at a rate of about 1-5 m/min.

Sample 14 was made by processing Control Absorbent II through an RKA process in which the toothed roll had teeth having the dimensions shown in FIGS. 24-27, as described above. The spunbond PP side of Control Absorbent II faced the RKA roll of the apparatus. The mating roll was an un-toothed roll, that is, a roll having circumferentially extending ridges and grooves, similar to that shown in FIG. 6 above at a DOE of about 6.35 mm (about 0.250 inch). The RKA process was carried out at a temperature of 350 degrees F. at a rate of about 1-5 m/min.

Sample 15 was made by processing Control Absorbent II through an RKA process in which the toothed roll had teeth having the dimensions shown in FIGS. 24-27 as described above. The spunbond PP side of Control Absorbent II faced the RKA roll of the apparatus. The mating roll was an un-toothed roll, that is, a roll having circumferentially extending ridges and grooves, similar to that shown in FIG. 6 above at a DOE of about 6.35 mm (about 0.250 inch). The RKA process was carried out at room temperature at a rate of about 1-5 m/min.

Sample 16 was made by processing Control Absorbent II through a SELF'ing process in which the toothed roll had teeth having the dimensions as described with respect to Sample 5 above. The spunbond PP side of Control Absorbent II faced the SELF roll of the apparatus. The mating roll was an un-toothed roll, that is, a roll having circumferentially extending ridges and grooves, similar to that shown in FIG. 6 above at a DOE of about 1.9 mm (about 0.075 inch). The process was carried out at room temperature at a rate of about 1-5 m/min.

Sample 17 was made by processing Control Absorbent II through a SELF'ing process in which the toothed roll had teeth having the dimensions as described with respect to Sample 5 above. The spunbond PP side of Control Absorbent II faced the SELF roll of the apparatus. The mating roll was an un-toothed roll, that is, a roll having circumferentially extending ridges and grooves, similar to that shown in FIG. 6 above at a DOE of about 1.9 mm (about 0.075 inch). The process was carried out at a temperature of 300 degrees F. at a rate of about 1-5 m/min.

Sample 18 was made by processing Control Absorbent II through a SELF'ing process in which the toothed roll had teeth having the dimensions as described with respect to Sample 5 above. The spunbond PP side of Control Absorbent II faced the SELF roll of the apparatus. The mating roll was an un-toothed roll, that is, a roll having circumferentially extending ridges and grooves, similar to that shown in FIG. 6 above at a DOE of about 1.65 mm (about 0.065 inch). The process was carried out at room temperature at a rate of about 1-5 m/min.

Sample 19 was made by processing Control Absorbent II through two separate inter-engaging rollers. First, Control Absorbent II was processed at room temperature through the nip of a ring roller having a pitch of about 1.016 mm (about 0.040 inch), and a DOE of about 1.016 mm (about 0.040 inch). Next, the ring rolled web was processed through an RKA process in which the toothed roll had teeth having the dimensions shown in FIGS. 31-34. The mating roll was an un-toothed roll, that is, a roll having circumferentially extending ridges and grooves, similar to that shown in FIG. 6 above at a DOE of about 1.143 mm (about 0.045 inch). The RKA process was carried out at a temperature of 220 degrees F. at a rate of about 1-5 m/min.

Sample 20 was made by processing Control Absorbent II through two separate inter-engaging rollers. First, Control Absorbent II was processed at room temperature through the nip of a micro-SELF roller having a pitch of about 1.524 mm (about 0.060 inch), a DOE of about 1.9 mm (about 0.075 inch), and at room temperature. The spunbond PP side of Control Absorbent II faced the ring roll (non-toothed roll) of the apparatus. Next, the micro-SELF'ed web was processed through an RKA process in which the toothed roll had teeth having the dimensions shown in FIGS. 31-34. The spunbond PP side of Control Absorbent II faced the RKA roll of the apparatus. The mating roll was an un-toothed roll, that is, a roll having circumferentially extending ridges and grooves, similar to that shown in FIG. 6 above at a DOE of about 2.16 mm (about 0.085 inch). The RKA process was carried out at a temperature of 300 degrees F. at a rate of about 1-5 m/min.

Sample 21 was made by processing Control Absorbent II through two separate inter-engaging rollers. First, Control Absorbent II was processed at room temperature through the nip of a micro-SELF roller having a pitch P of about 1.52 mm (about 0.060 inch), a DOE of about 1.9 mm (about 0.075 inch), and at room temperature. The spunbond PP side of Control Absorbent II faced the ring roll (non-toothed roll) of the apparatus. Next, the micro-SELF'ed web was processed through an RKA process in which the toothed roll had teeth having the dimensions shown in FIGS. 24-27. The spunbond PP side of Control Absorbent II faced the RKA roll of the apparatus. The mating roll was an un-toothed roll, that is, a roll having circumferentially extending ridges and grooves, similar to that shown in FIG. 6 above at a DOE of about 2.54 mm (about 0.100 inch). The RKA process was carried out at a temperature of 300 degrees F. at a rate of about 1-5 m/min.

As can be seen in Table 2, in almost all cases the capacity efficiency in grams (of absorbed fluid) per gram (of absorbent material) capacity, the permeability and the flow rate, all increased significantly, as did the capillary pressure in most cases. All these improvements are a result of simply processing a web material through the nip of a pair of inter-engaging rollers as described above. Therefore, there is no new material content or new composition that would increase costs associated with the much better fluid acquisition properties.

As shown above in Tables 1 and 2, processing the airlaid webs by the web deforming methods shown can have an immediate beneficial effect on the fluid handling properties of the web material. Without being bound by theory it is believed that this beneficial effect is due to the disruption of fibers in closely spaced discrete locations that produces discrete, but relatively closely spaced, regions of high or low permeability (depending on the specific web deformation process) surrounded by regions of low or high permeability, respectively. For example, in the example of ring rolling, the nature of the process is to produce rows of high density, high capillarity material, separated by rows of low density, low capillarity materials. While it is recognized that ring rolling is well known in the art, it is believed that the application of ring rolling to air laid materials is a new application providing for new and beneficial results in the art of absorbent core materials.

In addition to the benefits observed when individual webs are processed as shown in Tables 1 and 2, additional surprising and unexpected benefits can be achieved when webs processed by one or more of the web deforming processes described above are combined with other webs so processed, or processed by different web deforming processes. The present invention is particularly valuable in the context of sanitary napkins when one of the processed webs is used as a secondary topsheet and one of the webs is used as an absorbent core. The nomenclature "secondary topsheet" and "absorbent core" is not to be limiting. That is, the secondary topsheet can be considered to be an absorbent core also, but the term is used herein in its normal sense as developed in the art of sanitary napkins as a material used under and adjacent to a topsheet and having properties to move fluid away from the topsheet and into the absorbent core. That is, while a secondary topsheet can have absorbent properties, it is not intended to keep fluid retained but is intended to give up fluid to an absorbent storage medium, e.g., an absorbent core material, which absorbent core material is intended to retain fluid securely to ensure fluid does not return to the skin of the wearer.

The beneficial properties of the present invention can be illustrated with reference to Table 3. In Table 3 is shown fluid handling properties of a variety of combinations of web materials from Tables 1 and 2, i.e., the web materials having been deformed by one or more of the processes described above. In Table 3, each combination of web materials from Tables 1 and 2 was tested in a configuration to model a sanitary napkin, and each sample was tested with an apertured formed film web of the type disclosed in U.S. Pat. No. 4,629,643 issued to Curro et al. Dec. 16, 1986 and as marketed by The Procter & Gamble Co. on its line of ALWAYS® brand sanitary napkins.

Therefore, for each Sample in Table 3, the structure tested was a layered structure comprising, in order, an apertured formed film topsheet, secondary topsheet (STS) of Core II, and an absorbent core of Core I. Table 3 designates the particular air laid fibrous structures by reference to their respective sample numbers in Tables 1 and 2 above.

TABLE 3

Fluid Handling Properties of Combined Modified Airlaid Fibrous Absorbent Cores I and II

| Sample No. | Core I/Core II | Free Gush Run-off (%) | Acquisition (ml/sec) | Rewet Pressure (psi) | HGW Retained Capacity (g) |
|---|---|---|---|---|---|
| 22 | Sample 7/sample 1 | 47 | 0.06 | 0.86 | 25 |
| 23 | Sample 12/sample 1 | 39 | 0.07 | 1.62 | 26 |
| 24 | Sample 12/sample 2 | 34 | 0.10 | 1.61 | 26 |
| 25 | Sample 13/sample 2 | 40 | 0.19 | 1.36 | 30 |
| 26 | Sample 14/sample 2 | 35 | 0.11 | 1.19 | 28 |
| 27 | Sample 10/sample 1 | 37 | 0.09 | 1.07 | 29 |
| 28 | Sample 10/sample 2 | 28 | 0.13 | 0.87 | 29 |
| 29 | Sample 21/sample 2 | 38 | 0.11 | 0.82 | 27 |
| 30 | Sample 8/sample 1 | 52 | 0.07 | 1.00 | 26 |
| 31 | Sample 8/sample 2 | 37 | 0.12 | 0.96 | 26 |
| 32 | Sample 19/sample 1 | 40 | 0.06 | 1.10 | 26 |
| 33 | Sample 19/sample 2 | 35 | 0.08 | 0.88 | 27 |

As shown in Table 3, the 2-layer absorbent cores of the present invention (as shown in Samples 23-33) can break the permeability versus capillarity pressure tradeoff, by delivering relatively higher permeability (as shown by Free Gush Run-off, Acquisition speed, and Retained Capacity) without a significant decrease in capillary pressure (as shown by Rewet Pressure) compared to the Control (Sample 22).

The web of the present invention, used as an absorbent core in an absorbent product, exhibits properties that appear to have uncoupled the permeability versus capillarity pressure tradeoff. Without being bound by theory, it is believed that this apparent uncoupling is due to the creation of structures that have the effect of providing fluid handling properties in both of the tradeoff areas. For example, it is believed that the processes disclosed produce discrete locations of greater void volume, which, particularly in multiple layer cores permits the core materials to exhibit desirable benefits of both properties. The greater void volume in a fibrous material can result in greater permeability. These regions of greater permeability are relatively closely spaced, separated by the unmodified regions of the web, such regions exhibiting relatively lower permeability but relatively high capillary pressure. Thus, fluid impinging on the core, such as menses absorbed through a topsheet of an absorbent article during use, is presented with the possibility of both fluid dynamics, high permeability and high capillarity pressure. In effect, the fluid dynamics of such cores can be the result of taking advantage of the best of both material properties.

The material properties of the core of the present invention, whether single core or multiple core, can be further enhanced by additional core layers, or additional layers of material in a given core material. That is, for example, additional airlaid webs can be modified by the methods disclosed herein and added in layered relationship with the other two or more. As well, any one of the airlaid webs can itself be a layered structure exhibiting therein a Z-direction gradient in fluid handling properties. For example, for any one of the absorbent cores disclosed herein, including airlaid webs, the core can exhibit a Z-direction density gradient from low density on one side of the web to relatively high density on the other. Likewise, permeability, capillarity, fiber type and size, and other physical properties can be varied in various combinations within a layered web, such that a Z-direction gradient of virtually any physical property of the web can be envisioned as being useful in the present invention.

In one embodiment of a layered absorbent core, such as a layered airlaid web, it is contemplated that one layer could be designed to fracture upon treatment by the processes described herein, while other layer(s) do not. For example, a middle layer of a three layer airlaid web could comprise a material, such as a fibrous material, which fractures at low levels of strain, such that upon application of stress by the methods described herein, the middle layer fractures to form discrete, spaced apart apertures, while the remaining layers do not. In like manner a layer of a multi-layer web could be rendered into strips.

In one embodiment of a layered absorbent core, it is contemplated that a laminate could be formed in which one or more of the layers is a non-fibrous material, such as a foam or film web. For example, an absorbent core of the present invention can comprise, or be combined with, an absorbent foam material, such as high internal phase emulsions (HIPE) foams.

In one embodiment, the pattern of modification, such as by teeth on a SELF roll, can be varied across the width of the web being modified. For example, the rolls of a SELF process can be designed such that the pitch P of the teeth and grooves varies across the width of the rolls, and, consequently, across the width of the web. In this manner, for example, an absorbent core can be produced in which the central region corresponding to the longitudinal centerline region of an absorbent article, can have a pattern of ridges, tufts, apertures, or other feature, that is different from either or both side regions.

Figure 39:
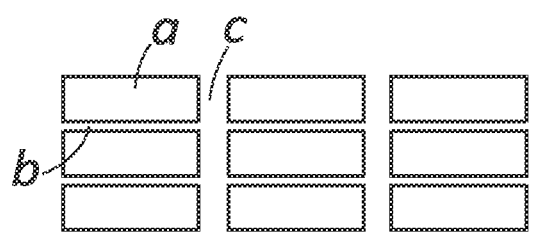
FIG. 39 is a schematic representation of a web of the present invention.
Figure 40:
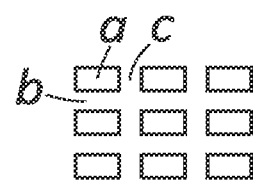
FIG. 40 is a schematic representation of a web of the present invention.

A schematic representation of two cores of the present invention for the purpose of illustrating density variation is shown in FIGS. 39 and 40. FIG. 39 shows a schematic representation of Sample 2 as detailed above with respect to Table 1. FIG. 40 shows a schematic representation of Sample 10 as detailed above with respect to Table 2. For both schematic representations, the out of plane, localized Z-direction deformations of the base web are indicated as rectangles. The rectangles shown are approximate representations of the relative X-Y boundaries of the Z-direction deformations, where X and Y can correspond to the cross-direction (CD) and machine-direction (MD), respectively. The rectangles show approximate representations of the "tent-like" rib-like elements of Sample 2, and the tufts of Sample 10, each of which can have a distinct aspect ratio of length divided by width, the aspect ratio of at least about 1.5 to 1, or 1.7 to 1, or 2.0 to 1 or 2.7 to 1, or 3 to 1, or 5 to 1, or 10 to 1, and including all numerical values between 1.5 and 10 in increments of one-tenth. The dimensions and shape of rectangles as well as the spacing of adjacent rectangles can be produced using visual imaging techniques, as is known in the art.

As shown in FIG. 39, rib-like elements indicated as "a" can be about 5.5 mm long and about 2 mm wide. Each element can be separated from adjacent elements in the CD by a region indicated as "b" which can be about 0.6 mm Each element can be separated from adjacent elements in the MD by a region indicated as "c" which can be about 1.3 mm Density measurements of the various regions "a", "b", and "c" show that SELF'ing of a nonwoven web, such as a fibrous airlaid web, can make relatively low density out-of-plane deformations. In the embodiment depicted in FIG. 39, the base material had a density of about 0.221 g/cc, region "a" had a density of about 0.128 g/cc, region "b" had a density of about 0.199 g/cc, and region "c" had a density of about 0.226 g/cc.

As shown in FIG. 40, tuft elements indicated as "a" can be about 1.7 mm long and about 1 mm wide. Each tuft element can be separated from adjacent elements in the CD by a region indicated as "b" which can be about 0.6 mm Each element can be separated from adjacent elements in the MD by a region indicated as "c" which can be about 1.2 mm Density measurements of the various regions "a", "b", and "c" show that micro-SELF'ing of a nonwoven web, such as a fibrous airlaid web, can make low density out-of-plane deformations. In the embodiment depicted in FIG. 40, the base material had a density of about 0.088 g/cc, region "a" had a density of about 0.0.072 g/cc, region "b" had a density of about 0.0.093 g/cc, and region "c" had a density of about 0.0.101 g/cc.

It is understood that the density values described above with respect to Samples 2 and 10 shown in FIGS. 39 and 40 are approximate, and the density values can vary depending on the base material properties, the process used to make Z-direction deformations, and other material and process variables. In general, it is believed that for airlaid webs having at least a portion of fibers being cellulosic fibers, that a density difference between the density of the base web and the density of the Z-direction deformation of at least about 18% to about 50% is beneficial for the present invention. The density difference between the density of the base web and the density of the Z-direction deformation can be 20%, 30%, 40% or greater than 50%. The density difference is believed to be most beneficial when the density of the Z-direction deformation is less than the density of the base material. The density of the base material can be considered to be essentially the same as the density of region "c" in FIGS. 39 and 40 in a web processed by the methods of the present invention.

It is understood that the density values provided herein are values for uncompressed webs processed to make absorbent cores as described herein. The absorbent cores described herein may be used in folded, compressed, packaged, and/or stored disposable absorbent articles. Therefore, the as-used density differences may be different than the as-made density differences. Therefore, it is believed that an absorbent core material used in a packaged disposable absorbent article can exhibit a density difference between the density of the regions between Z-direction deformations (e.g., the regions noted as "b" and "c" in FIGS. 39 and 40) and the density of the Z-direction deformation can be 5%, 10%, 20%, 30%, or greater than 40%. Currently it is believed that an airlaid nonwoven absorbent core comprising cellulosic fibers is most beneficial when the density differences above are due to the density of the Z-direction deformations being relatively lower than the density of the regions between Z-direction deformations.

The density data as discussed above with respect to Samples 2 and 10 shown in FIGS. 39 and 40 were obtained by using a MicroCT40 (Scanco Medical, Bassersdorf, Switzerland) x-ray scanner at high resolution, 35 KeV energy, 300 micron integration time and 10 averaging. A field of view of 20×20 mm in X/Y and 2-3 mm in Z (depending on the sample) with an x/y/z resolution of 10 microns in all directions was used for the tomographic reconstruction of the datasets. Each dataset was approximately 2048×2048 in x/y and around 200-300 slices in the z direction. After removing the sample holder from the field of view, the remaining stack of slices was analyzed as follows:

1) A threshold of 1000 was used to distinguish between a fiber and background.
2) The Thickness at each x/y point was determined by finding the first fiber (any pixel>1000) along the Z direction (perpendicular to the wipe surface) and the last fiber along the Z direction. The difference between these two Z values provided the thickness at each location in X/Y. This image was saved in TIFF format.
3) The Basis Weight image at each x/y point was determined by summing all the values>1000 along the Z direction. This image was saved in TIFF format.
4) The Density image at each x/y point was determined to be the value of the basis weight image at (X,Y) divided by the value of the thickness image at (X,Y). Images of 0 thickness were set to 0 in the Density image. This image was saved in TIFF format.
5) The user then selects regions within the thickness image. Each region is labeled either thick or thin. The thickness mean and standard deviation, basis weight mean and standard deviation, and density mean and standard deviation are then calculated for the region chosen (in each respective image) and reported out as desired, for example to a .csv file to an Excel® spreadsheet.

Test Methods

1. Artificial Menstrual Fluid Preparation

For each of the tests using Artificial Menstrual Fluid (AMF), prepare as follows:

Step 1: Dilute 10 ml of reagent grade 85-95% w/w lactic acid to 100 ml with distilled water. Label as 10% v/v lactic acid.

Step 2: Add 11.76 g of reagent grade 85% w/w potassium hydroxide (KOH) to a flask and dilute to 100 ml with distilled water. Mix until completely dissolved. Label as 10% w/v KOH.

Step 3: Add 8.5 g sodium chloride and 1.38 g of hydrous monobasic sodium phosphate to a flask and dilute to 1000 ml with distilled water. Mix until completely dissolved. Label as monobasic sodium phosphate solution.

Step 4: Add 8.5 g sodium chloride and 1.42 g anhydrous dibasic sodium phosphate to a flask and dilute to 1000 ml with distilled water. Mix until completely dissolved. Label as dibasic sodium phosphate solution.

Step 5: Add 450 ml of dibasic phosphate solution to a 1000 ml beaker and add monobasic sodium phosphate solution until the PH is lowered to 7.2±0.1. Label as phosphate solution.

Step 6: Mix 460 ml of phosphate solution and 7.5 ml of 10% KOH in a 1000 ml beaker. Heat Solution to 45° C.±5° C. and then add 28 sterilized gastric mucin (ICN Biomedical Inc., Cleveland, Ohio). Continue heating for 2.5 hours to completely dissolve the gastric mucin. Allow the solution to cool to less than 40° C. and then add 1.8±0.2 ml of 10% v/v lactic acid solution. Autoclave the mixture at 121° C. for 15 minutes, then allow to cool to room temperature. Mucous mixture should be used within 7 days. Label as gastric mucin solution.

Step 7: Mix 500 ml of gastric mucin solution and 500 ml of fresh, sterile defibrinated sheep blood (Cleveland Scientific, American Biomedical, Bath, Ohio) in a beaker. Label as artificial menstrual fluid. Store refrigerated and use within 7 days.

2. Absorption Capillary Potential and Desorption Capillary Potential

Absorption Capillary Potential, also referred to as absorption energy, and Desorption Capillary Potential, also referred to as desorption energy, can be determined by evaluating capillary work potential for each tested material.

The ability of absorbent materials to absorb or desorb fluid via capillary potential is measure by the Capillary Work Potential.

Step 1: A TRI Autoporosimeter from TRI, Princeton, N.J., is used to measure percentage of fluid saturation as a function of pressure of the absorbent core I and II samples listed in table 1 and 2.

Step 2: The testing fluid used here is n-hexadecane.

Step 3: There are three testing cycles to generate three capillary pressure vs. percent saturation curves:
1) 1st Absorption with dry material (imbibition)
2) Draining
3) 2nd Absorption with wet material Step 4: The Absorption Capillary Potential (absorption Capillary Work Potential (CWP)) is calculated by the integration of the 1st absorption curve of capillary potential as a function of uptake volume.

$$W = \int P_{cap(CV)} dCV \text{ (mJ/m}^2\text{)}$$

Where CV is the measured cumulative uptake volume (convertible to saturation)

Step 5: The Desorption Capillary Pressure (desorption Capillary Work Potential (CWP)) is calculated by the integration of the draining curve of capillary pressure as a function of uptake volume.

$$W = \int P_{cap(CV)} dCV \text{ (mJ/m}^2\text{)}$$

Where CV is the measured cumulative uptake volume (convertible to saturation)

3. Permeability (Darcy's) and Flow Rate (g/sec)

Permeability is determined from the mass flow rate of any given fluid through a porous medium. The procedure for determining both is as follows:

Step 1: A through plane permeability device is used to automatically dispense and measure flow of liquid through a sample by monitoring the distance a column of water drops in relation to time and pressure measure.

Step 2: The pressure drop determines the mass flow rate of a fluid through a porous medium across the sample.

Step 3 (for flow rate of Table 1): The flow rate is determined at a variable pressure in the falling hydro head mode using a salt solution containing 2.75% Calcium Chloride as the fluid for all of the Absorbent I samples in Table 1.

Step 3 (for flow rate of Table 2): The flow rate is determined at constant pressure using the constant hydro head mode using distilled/de-ionized water as the fluid for all of the Absorbent II samples in Table 2.

Step 4: Darcy permeability and Flow Rate is calculated by the equations below:

$$F = k(A/\mu)(\Delta p/l) \quad (1)$$

$$K = 9.87 \times 10^{-7} k \quad (2)$$

Where: F=flow Rate (g/s)
k=permeability of the porous material (m$^2$)
A=Cross sectional area available for flow (m$^2$)
l=Thickness of the material (m)
μ=Fluid viscosity (cP)
Δp=Pressure Drop (cm H$_2$O)
K=permeability (Darcy's)

4. Free Gush Run-Off (%)

This test measures the weight percentage of fluid not being acquired (% run-off) by an absorbent pad. The protocol includes loading 10 ml of artificial menstrual fluid (AMF) on an unloaded (fresh) sanitary napkin which is placed at 15° incline angle in the CD direction (i.e., the width of a sanitary napkin in a flat condition). Reported values are the average of N=3.

AMF Preparation:
  Condition AMF at 73±4° F. (23±2° C.) for 2 hours before drawing fluid for testing.

Sample Preparation and Apparatus:
Step 1: Pre-stress each pad to be tested by: holding the ends of the pad and twisting it 10 times followed by folding the pad approximately 90 degrees to make the ends meet 10 times.
Step 2: Allow samples to be equilibrated for at least two hours in a room conditioned to 73±4° F. (23±2° C.) temperature and 50±4% relative humidity prior to testing.
Step 3: Mark the center point at the narrowest width of the pad as the target fluid loading point. The apparatus includes a sample holder ring stand with 15° fixed incline base, a fluid delivery separatory funnel with a nozzle, and a run-off basin.

Procedures:
Step 1: Weigh each sample pad to be tested.
Step 2: Place the pad onto the sample holder in the CD direction with 15° incline angle and adjust the fluid delivery nozzle to be centered over the marked center point and 0.5 inches (12.7 mm) above the pad surface.
Step 3: Fill 10 ml of AMF into the separatory funnel.
Step 4: Quickly open the valve of the funnel and allow the 10 ml fluid drained completely from the funnel onto the pad surface in 3 seconds or less.
Step 5: Weigh the wet pad
Step 6: Subtract the pad's dry weight from the wet weight to determine the amount of fluid absorbed. Subtract this number from 10 to get the amount of fluid not absorbed (run-off). Then divide the run-off amount by 10 and multiply the result times 100 to report as the 10 ml Free Gush Run-Off.

5. HGW Retained Capacity

HGW is an absorbency test that measures the uptake of fluid by an absorbent pad as a function of time.

AMF Preparation:
  Condition AMF at 73±4° F. (23±2° C.) for 2 hours before drawing fluid for testing.

Sample Preparation and Apparatus:
  Allow sample pads to be equilibrated for at least two hours in a room conditioned to 73±4° F. (23±2° C.) temperature and 50±4% relative humidity prior to testing.

Procedure:
Step 1: Place the sample pad upside (top sheet side) down horizontally in a holder basket suspended from an electronic balance. Supply desired confining air pressure for either 0.06 psi or 0.25 psi to the sample holder basket.
Step 2: A fluid loading column's tube, containing AMF and connected to a fluid reservoir at zero hydrostatic head relative to the pad, is allowed to contact the topsheet of the pad as a point source and the increase in weight of the sample is used as a fluid uptake versus time.
Step 3: The test proceeds until the pad is fully saturated.
Step 4: 7-piles of filter paper are placed over the saturated pad and a load of 0.25 psi (17.6 g/cm2), followed by 1.0 psi (70.3 g/cm2) is applied to squeeze-out the fluid.
Step 5: HGW Retained Capacity is the weight in grams of fluid remaining in the sample post squeeze-out.

Reported values are the average of N=3.

6. Rewet Pressure

Rewet Pressure is the amount of pressure needed to cause liquid to emerge back through a previously wetted topsheet from a wet underlying absorbent core.

AMF Preparation:
  Condition AMF at 73±4° F. (23±2° C.) for 2 hours before drawing fluid for testing.

Sample Preparation and Apparatus:
Step 1: Allow sample pads to be tested to equilibrate for at least two hours in a room conditioned to 73±4° F. (23±2° C.) temperature and 50±4% relative humidity prior to testing.
Step 2: The apparatus used to measure the loading force is a Tensile Tester with light duty jaws such as EME model 607, model 627, or model 599A, available from the EME Co., Newbury, Ohio. It is equipped with a sample holder base plate and a compression sensor foot which are also available form EME.

Procedure:
Step 1: Place the sample pad topsheet side up and place a Plexiglas fluid loading strike through cap, with a center hole, on the center of the pad.
Step 2: Dispense 7.5±0.3 ml of AMF through the center hole of the strike through cap in 5 second or less.
Step 3: As soon as the pad completely absorbs the fluid, remove the strike through cap, then start the time for 5 minute.
Step 4: Place the loaded sample pad onto the sample holder base plate and center the compression sensor foot directly above the stain area.
Step 5: At the end of the 5 minute, start the tensile tester. The cross head should move down to compression the sample until the fluid is detected.
Step 6: The rewet pressure is the compression force divided by the area of the compression sensor foot.

Reported values are the average of N=3.

7. Acquisition Rate (ml/sec)

This test measures gush acquisition rate, i.e., how fast the absorbent pad acquires fluid.

AMF Preparation:
  Condition AMF at 73±4° F. (23±2° C.) for 2 hours before drawing fluid for testing.

Sample Preparation:
  Allow test pad samples to be equilibrated for at least two hours in a room conditioned to 73±4° F. (23±2° C.) temperature and 50±4% relative humidity prior to testing.

Procedures:
Step 1: Place a 4 inch square block with a 1 inch by 0.6 inch opening (generally oval in shape) over the center of the sample pad to be tested. Add sufficient weight to the block to achieve a 0.25 psi pressure, without obstructing opening.
Step 2: Add AMF through the top of the opening to the sample pad at a rate of 2 ml/hr for 2.25 hour via a Low Flow Syringe Pump from Harvard Apparatus, Southnatick, Mass.
Step 3: Then, add 3 ml AMF at once through the opening to the sample pad using a Eppendorf Maxipipetter from Fisher Scientific. Time the interval between the first drop of 3 ml AMF and no AMF is visible on the top surface of the sample.
Step 4: Calculate the Acquisition rate in ml/sec by dividing the amount (3 ml) by the time in seconds measured in Step 3.

Reported values are the average of N=3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin comprising a topsheet joined to a backsheet and having an absorbent core disposed therebetween, said absorbent core having a longitudinal centerline and comprising a first absorbent fibrous web material having a pattern of a plurality of pairs of adjacent ribs and valleys extending in a direction substantially parallel to the longitudinal centerline, the plurality of pairs of adjacent ribs and valleys exhibiting localized stretching in intermediate sections of the web between the adjacent ribs and valleys, said ribs and valleys defining a network of channels, said channels defining void regions between the first absorbent fibrous web material and an adjacent layer of said sanitary napkin, said pattern extending laterally across said first absorbent fibrous web material.

2. The sanitary napkin of claim 1, wherein said first absorbent fibrous web material is selected from the group consisting of meltblown, spunbond, carded, wetlaid, and airlaid webs.

3. The sanitary napkin of claim 2, wherein said first absorbent fibrous web material comprises airlaid fibers.

4. The sanitary napkin of claim 1, wherein said absorbent core comprises cellulosic fibers.

5. The sanitary napkin of claim 1, wherein said absorbent core comprises absorbent gelling materials.

6. The sanitary napkin of claim 1, further comprising a secondary topsheet, said secondary topsheet comprising a second absorbent fibrous web material disposed adjacent to and between said topsheet and said absorbent core.

7. The sanitary napkin of claim 6, wherein said second absorbent fibrous web material is an airlaid web comprising cellulosic fibers.

8. The sanitary napkin of claim 6, wherein said second absorbent fibrous web material comprises a plurality of apertures.

9. The sanitary napkin of claim 1, wherein said absorbent core comprises a layered, airlaid nonwoven fibrous web having a plurality of discrete layers, one of said discrete layers comprising a different type of fiber or blend of fibers with respect to another of said discrete layers.

10. A sanitary napkin comprising in layered order a topsheet, a secondary topsheet, an absorbent core having a longitudinal centerline, and a backsheet, at least said topsheet and backsheet being joined, and wherein said secondary topsheet is an absorbent fibrous web having a pattern of a plurality of pairs of adjacent of ribs and valleys extending in a direction substantially parallel to the longitudinal centerline, the plurality of pairs of adjacent ribs and valleys exhibiting localized stretching in intermediate sections of the web between the adjacent ribs and valleys, said ribs and valleys defining a network of channels, said channels defining void regions between the absorbent fibrous web material and said topsheet, said pattern extending laterally across said first absorbent fibrous web material.

11. The sanitary napkin of claim 10, wherein said absorbent fibrous web material is selected from the group consisting of meltblown, spunbond, carded, wetlaid, and airlaid webs.

12. The sanitary napkin of claim 11, wherein said absorbent fibrous web material comprises airlaid fibers.

13. The sanitary napkin of claim 10, wherein said absorbent core comprises cellulosic fibers.

14. The sanitary napkin of claim 10, wherein said absorbent core comprises absorbent gelling materials.

15. The sanitary napkin of claim 10, wherein said secondary topsheet is an airlaid web comprising cellulosic fibers.

16. The sanitary napkin of claim 10, wherein said secondary topsheet comprises a plurality of apertures.

17. The sanitary napkin of claim 10, wherein said absorbent core comprises a layered, airlaid nonwoven fibrous web having a plurality of discrete layers, one of said discrete layers comprising a different type of fiber or blend of fibers with respect to another of said discrete layers.

18. The sanitary napkin of claim 10, wherein said secondary topsheet comprises a layered, airlaid nonwoven fibrous web having a plurality of discrete layers, one of said discrete layers comprising a different type of fiber or blend of fibers with respect to another of said discrete layers.

19. An absorbent article comprising in layered order a topsheet, a secondary topsheet, an absorbent core having a longitudinal centerline, and a backsheet, at least said topsheet and said backsheet being joined, the layers being in a generally flat, layered relationship, said secondary topsheet comprising a first airlaid absorbent fibrous web comprising cellulosic fibers, and wherein said absorbent core comprises a second airlaid absorbent fibrous web material comprising cellulosic fibers and having a pattern of a plurality of pairs of adjacent ribs and valleys extending in a direction substantially parallel to the longitudinal centerline, the plurality of pairs of adjacent ribs and valleys exhibiting localized stretching in intermediate sections of the web between the adjacent ribs and valleys, said ribs and valleys defining a network of channels, said channels defining void regions between the first airlaid absorbent fibrous web material and said second airlaid absorbent fibrous web material, said pattern extending laterally across said first absorbent fibrous web material.

20. The absorbent article of claim 19, wherein said absorbent article is a sanitary napkin.

* * * * *